(12) United States Patent
State et al.

(10) Patent No.: US 12,262,960 B2
(45) Date of Patent: *Apr. 1, 2025

(54) AFFECTED REGION DISPLAY ASSOCIATED WITH A MEDICAL DEVICE

(71) Applicant: InnerOptic Technology, Inc., Hillsborough, NC (US)

(72) Inventors: Andrei State, Chapel Hill, NC (US); Luv Kohli, Durham, NC (US); Sharif Razzaque, Boulder, CO (US); Brian Heaney, Durham, NC (US)

(73) Assignee: InnerOptic Technology, Inc., Hillsborough, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/340,717

(22) Filed: Jun. 23, 2023

(65) Prior Publication Data

US 2024/0041536 A1 Feb. 8, 2024

Related U.S. Application Data

(63) Continuation of application No. 17/071,459, filed on Oct. 15, 2020, now Pat. No. 11,684,429, which is a
(Continued)

(51) Int. Cl.
*A61B 34/20* (2016.01)
*A61B 34/00* (2016.01)
(Continued)

(52) U.S. Cl.
CPC ............. *A61B 34/20* (2016.02); *G06T 19/00* (2013.01); *A61B 2034/2048* (2016.02);
(Continued)

(58) Field of Classification Search
CPC . A61B 34/20; A61B 34/25; A61B 2034/2051; A61B 2034/2048;
(Continued)

(56) References Cited

U.S. PATENT DOCUMENTS

| 3,556,079 A | 1/1971 | Omizo |
| 4,058,114 A | 11/1977 | Soldner |

(Continued)

FOREIGN PATENT DOCUMENTS

| EP | 0 427 358 | 5/1991 |
| JP | S63-290550 A | 11/1988 |

(Continued)

OTHER PUBLICATIONS

U.S. Appl. No. 11/828,826 including without limitation Office Actions, Amendments, Remarks, and any other potentially relevant documents, filed Jul. 26, 2007, Keller et al.

(Continued)

*Primary Examiner* — Ryan M Gray
(74) *Attorney, Agent, or Firm* — Knobbe, Martens, Olson & Bear, LLP

(57) ABSTRACT

A system and method for providing image guidance for placement of one or more medical devices at a target location. The system can be used to determine one or more affected regions corresponding to the operation of one or more medical devices and display at least a portion of the one or more affected regions. The affected regions can correspond to predicted affected regions and/or dynamic affected regions and can be based at least in part on a variance parameter of the medical device.

20 Claims, 9 Drawing Sheets

Related U.S. Application Data continuation of application No. 15/882,709, filed on Jan. 29, 2018, now Pat. No. 10,820,944, which is a continuation of application No. 14/872,930, filed on Oct. 1, 2015, now Pat. No. 9,901,406.

(60) Provisional application No. 62/059,077, filed on Oct. 2, 2014.

(51) Int. Cl.
*A61B 90/00* (2016.01)
*G06T 19/00* (2011.01)

(52) U.S. Cl.
CPC .............. *A61B 2034/2051* (2016.02); *A61B 2034/2055* (2016.02); *A61B 34/25* (2016.02); *A61B 2090/365* (2016.02); *A61B 2090/378* (2016.02); *G06T 2210/41* (2013.01)

(58) Field of Classification Search
CPC ...... A61B 2034/2055; A61B 2090/365; A61B 2090/378; G06T 19/00; G06T 2210/41
See application file for complete search history.

(56) References Cited

U.S. PATENT DOCUMENTS

| | | |
|---|---|---|
| RE30,397 E | 9/1980 | King |
| 4,249,539 A | 2/1981 | Vilkomerson et al. |
| 4,294,544 A | 10/1981 | Altschuler et al. |
| 4,390,025 A | 6/1983 | Takemura et al. |
| 4,407,294 A | 10/1983 | Vilkomerso |
| 4,431,006 A | 2/1984 | Trimmer et al. |
| 4,567,896 A | 2/1986 | Barnea et al. |
| 4,583,538 A | 4/1986 | Onik et al. |
| 4,620,546 A | 11/1986 | Aida et al. |
| 4,671,292 A | 6/1987 | Matzuk |
| 4,839,836 A | 6/1989 | Fonsalas |
| 4,862,873 A | 9/1989 | Yajima et al. |
| 4,884,219 A | 11/1989 | Waldren |
| 4,899,756 A | 2/1990 | Sonek |
| 4,911,173 A | 3/1990 | Terwillige |
| 4,945,305 A | 7/1990 | Blood |
| 5,076,279 A | 12/1991 | Arenson et al. |
| 5,078,140 A | 1/1992 | Kwoh |
| 5,078,142 A | 1/1992 | Siczek et al. |
| 5,095,910 A | 3/1992 | Powers |
| 5,109,276 A | 4/1992 | Nudelman et al. |
| 5,156,144 A | 10/1992 | Iwasaki et al. |
| 5,158,088 A | 10/1992 | Nelson et al. |
| 5,161,536 A | 11/1992 | Vikomerson et al. |
| 5,193,120 A | 3/1993 | Gamache et al. |
| 5,209,235 A | 5/1993 | Brisken et al. |
| 5,249,581 A | 10/1993 | Horbal et al. |
| 5,251,127 A | 10/1993 | Raab |
| 5,261,404 A | 11/1993 | Mick et al. |
| 5,265,610 A | 11/1993 | Darrow et al. |
| 5,271,400 A | 12/1993 | Dumoulin et al. |
| 5,307,153 A | 4/1994 | Maruyama et al. |
| 5,309,913 A | 5/1994 | Kormos et al. |
| 5,323,002 A | 6/1994 | Sampsell et al. |
| 5,371,543 A | 12/1994 | Anderson |
| 5,383,454 A | 1/1995 | Bucholz |
| 5,394,875 A | 3/1995 | Lewis et al. |
| 5,411,026 A | 5/1995 | Carol |
| 5,433,198 A | 7/1995 | Desai |
| 5,433,739 A | 7/1995 | Sluijter |
| 5,443,489 A | 8/1995 | Ben-Haim |
| 5,446,798 A | 8/1995 | Morita et al. |
| 5,447,154 A | 9/1995 | Cinquin et al. |
| 5,452,024 A | 9/1995 | Sampsell |
| 5,457,493 A | 10/1995 | Leddy et al. |
| 5,474,073 A | 12/1995 | Schwartz et al. |
| 5,476,096 A | 12/1995 | Olstad et al. |
| 5,483,961 A | 1/1996 | Kelly et al. |
| 5,488,431 A | 1/1996 | Gove et al. |
| 5,489,952 A | 2/1996 | Gove et al. |
| 5,491,510 A | 2/1996 | Gove |
| 5,494,039 A | 2/1996 | Onik et al. |
| 5,503,152 A | 4/1996 | Oakley et al. |
| 5,505,204 A | 4/1996 | Picot et al. |
| 5,515,856 A | 5/1996 | Olstad et al. |
| 5,517,990 A | 5/1996 | Kalfas et al. |
| 5,526,051 A | 6/1996 | Gove et al. |
| 5,526,812 A | 6/1996 | Dumoulin et al. |
| 5,529,070 A | 6/1996 | Augustine et al. |
| 5,531,227 A | 7/1996 | Schneider |
| 5,532,997 A | 7/1996 | Pauli |
| 5,541,723 A | 7/1996 | Tanaka |
| 5,558,091 A | 9/1996 | Acker et al. |
| 5,568,811 A | 10/1996 | Olstad |
| 5,570,135 A | 10/1996 | Gove et al. |
| 5,579,026 A | 11/1996 | Tabata |
| 5,581,271 A | 12/1996 | Kraemer |
| 5,588,948 A | 12/1996 | Takahashi et al. |
| 5,608,468 A | 3/1997 | Gove et al. |
| 5,608,849 A | 3/1997 | King, Jr. |
| 5,611,345 A | 3/1997 | Hibbeln |
| 5,611,353 A | 3/1997 | Dance et al. |
| 5,612,753 A | 3/1997 | Poradish et al. |
| 5,625,408 A | 4/1997 | Matsugu et al. |
| 5,628,327 A | 5/1997 | Unger et al. |
| 5,629,794 A | 5/1997 | Magel et al. |
| 5,630,027 A | 5/1997 | Venkateswar et al. |
| 5,647,361 A | 7/1997 | Damadian |
| 5,647,373 A | 7/1997 | Paltieli et al. |
| 5,660,185 A | 8/1997 | Shmulewitz et al. |
| 5,662,111 A | 9/1997 | Cosman |
| 5,699,444 A | 12/1997 | Palm |
| 5,701,898 A | 12/1997 | Adam et al. |
| 5,701,900 A | 12/1997 | Shehada et al. |
| 5,726,670 A | 3/1998 | Tabata et al. |
| 5,728,044 A | 3/1998 | Shan |
| 5,758,650 A | 6/1998 | Miller et al. |
| 5,766,135 A | 6/1998 | Terwilliger |
| 5,784,098 A | 7/1998 | Shoji et al. |
| 5,792,147 A | 8/1998 | Evans et al. |
| 5,793,701 A | 8/1998 | Wright et al. |
| 5,797,849 A | 8/1998 | Vesely et al. |
| 5,806,521 A | 9/1998 | Morimoto et al. |
| 5,807,395 A | 9/1998 | Mulier et al. |
| 5,810,008 A | 9/1998 | Dekel et al. |
| 5,817,022 A | 10/1998 | Vesely |
| 5,820,554 A | 10/1998 | Davis et al. |
| 5,820,561 A | 10/1998 | Olstad et al. |
| 5,829,439 A | 11/1998 | Yokosawa et al. |
| 5,829,444 A | 11/1998 | Ferre et al. |
| 5,851,183 A | 12/1998 | Bodiolz |
| 5,870,136 A | 2/1999 | Fuchs et al. |
| 5,891,034 A | 4/1999 | Bucholz |
| 5,920,395 A | 7/1999 | Schulz |
| 5,961,527 A | 10/1999 | Whitmore, III et al. |
| 5,967,980 A | 10/1999 | Ferre et al. |
| 5,967,991 A | 10/1999 | Gardineer et al. |
| 5,991,085 A | 11/1999 | Rallison et al. |
| 6,016,439 A | 1/2000 | Acker |
| 6,019,724 A | 2/2000 | Gronningsaeter et al. |
| 6,048,312 A | 4/2000 | Ishrak et al. |
| 6,064,749 A | 5/2000 | Hirota et al. |
| 6,091,546 A | 7/2000 | Spitzer |
| 6,095,982 A | 8/2000 | Richards-Kortum et al. |
| 6,099,471 A | 8/2000 | Torp et al. |
| 6,108,130 A | 8/2000 | Raj |
| 6,122,538 A | 9/2000 | Sliwa, Jr. et al. |
| 6,122,541 A | 9/2000 | Cosman et al. |
| 6,160,666 A | 12/2000 | Rallison et al. |
| 6,167,296 A | 12/2000 | Shahidi |
| 6,181,371 B1 | 1/2001 | Maguire, Jr. |
| RE37,088 E | 3/2001 | Olstad et al. |
| 6,216,029 B1 | 4/2001 | Paltieli |
| 6,241,725 B1 | 6/2001 | Cosman |
| 6,245,017 B1 | 6/2001 | Hashimoto et al. |
| 6,246,784 B1 | 6/2001 | Summers et al. |
| 6,246,898 B1 | 6/2001 | Vesely et al. |

(56) References Cited

U.S. PATENT DOCUMENTS

| | | |
|---|---|---|
| 6,248,101 B1 | 6/2001 | Witmore, III et al. |
| 6,261,234 B1 | 7/2001 | Lin |
| 6,341,016 B1 | 1/2002 | Malione |
| 6,348,058 B1 | 2/2002 | Melken et al. |
| 6,350,238 B1 | 2/2002 | Olstad et al. |
| 6,352,507 B1 | 3/2002 | Torp et al. |
| 6,379,302 B1 | 4/2002 | Kessman et al. |
| 6,385,475 B1 | 5/2002 | Cinquin et al. |
| 6,442,417 B1 | 8/2002 | Shahidi et al. |
| 6,447,450 B1 | 9/2002 | Olstad |
| 6,456,868 B2 | 9/2002 | Saito et al. |
| 6,470,207 B1 | 10/2002 | Simon et al. |
| 6,471,366 B1 | 10/2002 | Hughson et al. |
| 6,477,400 B1 | 11/2002 | Barrick |
| 6,478,793 B1 | 11/2002 | Cosman et al. |
| 6,503,195 B1 | 1/2003 | Keller et al. |
| 6,511,418 B2 | 1/2003 | Shahidi et al. |
| 6,517,485 B2 | 2/2003 | Torp et al. |
| 6,518,939 B1 | 2/2003 | Kikuchi |
| 6,527,443 B1 | 3/2003 | Vilsmeier |
| 6,529,758 B2 | 3/2003 | Shahidi |
| 6,537,217 B1 | 3/2003 | Bjaerum et al. |
| 6,545,706 B1 | 4/2003 | Edwards et al. |
| 6,546,279 B1 | 4/2003 | Bova et al. |
| 6,547,777 B2 | 4/2003 | Di Resta et al. |
| 6,551,325 B2 | 4/2003 | Neubauer et al. |
| 6,570,566 B1 | 5/2003 | Yoshigahara |
| 6,575,969 B1 | 6/2003 | Rittman, III et al. |
| 6,579,240 B2 | 6/2003 | Bjaerum et al. |
| 6,587,711 B1 | 7/2003 | Alfano et al. |
| 6,591,130 B2 | 7/2003 | Shahidi |
| 6,592,522 B2 | 7/2003 | Bjaerum et al. |
| 6,594,517 B1 | 7/2003 | Nevo |
| 6,597,818 B2 | 7/2003 | Kumar et al. |
| 6,604,404 B2 | 8/2003 | Paltieli et al. |
| 6,616,610 B2 | 9/2003 | Steininger et al. |
| 6,626,832 B1 | 9/2003 | Paltieli et al. |
| 6,652,462 B2 | 11/2003 | Bjaerum et al. |
| 6,669,635 B2 | 12/2003 | Kessman et al. |
| 6,676,599 B2 | 1/2004 | Torp et al. |
| 6,689,067 B2 | 2/2004 | Sauer et al. |
| 6,695,786 B2 | 2/2004 | Wang et al. |
| 6,711,429 B1 | 3/2004 | Gilboa et al. |
| 6,725,082 B2 | 4/2004 | Sati et al. |
| 6,733,458 B1 | 5/2004 | Steins et al. |
| 6,764,449 B2 | 7/2004 | Lee et al. |
| 6,766,184 B2 | 7/2004 | Utzinger et al. |
| 6,768,496 B2 | 7/2004 | Bieger et al. |
| 6,775,404 B1 | 8/2004 | Pagoulatos et al. |
| 6,782,287 B2 | 8/2004 | Grzeszczuk et al. |
| 6,783,524 B2 | 8/2004 | Anderson et al. |
| 6,827,723 B2 | 12/2004 | Carson |
| 6,863,655 B2 | 3/2005 | Bjaerum et al. |
| 6,873,867 B2 | 3/2005 | Vilsmeier |
| 6,875,179 B2 | 4/2005 | Ferguson et al. |
| 6,881,214 B2 | 4/2005 | Cosman et al. |
| 6,895,268 B1 | 5/2005 | Rahn et al. |
| 6,915,150 B2 | 7/2005 | Cinquin et al. |
| 6,917,827 B2 | 7/2005 | Kienzle, III |
| 6,923,817 B2 | 8/2005 | Carson et al. |
| 6,936,048 B2 | 8/2005 | Hurst |
| 6,947,783 B2 | 9/2005 | Immerz |
| 6,968,224 B2 | 11/2005 | Kessman et al. |
| 6,978,167 B2 | 12/2005 | Dekel et al. |
| 7,008,373 B2 | 3/2006 | Stoianovici et al. |
| 7,033,360 B2 | 4/2006 | Cinquin et al. |
| 7,072,707 B2 | 7/2006 | Galloway, Jr. et al. |
| 7,077,807 B2 | 7/2006 | Torp et al. |
| 7,093,012 B2 | 8/2006 | Oltad et al. |
| 7,110,013 B2 | 9/2006 | Ebersole et al. |
| 7,171,255 B2 | 1/2007 | Holupka et al. |
| 7,209,776 B2 | 4/2007 | Leitner |
| 7,245,746 B2 | 7/2007 | Bjaerum et al. |
| 7,248,232 B1 | 7/2007 | Yamazaki et al. |
| 7,261,694 B2 | 8/2007 | Torp et al. |
| 7,313,430 B2 | 12/2007 | Urquhart et al. |
| 7,331,932 B2 | 2/2008 | Leitner |
| 7,351,205 B2 | 4/2008 | Szczech et al. |
| 7,379,769 B2 | 5/2008 | Piron et al. |
| 7,385,708 B2 | 6/2008 | Ackerman et al. |
| 7,392,076 B2 | 6/2008 | Moctezuma de la Barrera |
| 7,398,116 B2 | 7/2008 | Edwards |
| 7,466,303 B2 | 12/2008 | Yi et al. |
| 7,480,533 B2 | 1/2009 | Cosman et al. |
| 7,505,809 B2 | 3/2009 | Strommer et al. |
| 7,588,541 B2 | 9/2009 | Floyd et al. |
| 7,596,267 B2 | 9/2009 | Accomazzi et al. |
| 7,652,259 B2 | 1/2010 | Kimchy et al. |
| 7,662,128 B2 | 2/2010 | Salcudean et al. |
| 7,678,052 B2 | 3/2010 | Torp et al. |
| 7,728,868 B2 | 6/2010 | Razzaque et al. |
| 7,747,305 B2 | 6/2010 | Dean et al. |
| 7,797,032 B2 | 9/2010 | Martinelli et al. |
| 7,798,965 B2 | 9/2010 | Torp et al. |
| 7,833,168 B2 | 11/2010 | Taylor et al. |
| 7,833,221 B2 | 11/2010 | Voegele et al. |
| 7,846,103 B2 | 12/2010 | Cannon, Jr. et al. |
| 7,876,942 B2 | 1/2011 | Gilboa |
| 7,889,905 B2 | 2/2011 | Higgins et al. |
| 7,912,849 B2 | 3/2011 | Ohrn et al. |
| 7,920,909 B2 | 4/2011 | Lyon et al. |
| 7,962,193 B2 | 6/2011 | Edwards et al. |
| 7,976,469 B2 | 7/2011 | Bonde et al. |
| 8,023,712 B2 | 9/2011 | Ikuma et al. |
| 8,038,631 B1 | 10/2011 | Sanghvi et al. |
| 8,041,413 B2 | 10/2011 | Barbagli et al. |
| 8,050,736 B2 | 11/2011 | Piron et al. |
| 8,052,636 B2 | 11/2011 | Moll et al. |
| 8,066,644 B2 | 11/2011 | Sarkar et al. |
| 8,073,528 B2 | 12/2011 | Zhao et al. |
| 8,086,298 B2 | 12/2011 | Whitmore, III et al. |
| 8,135,669 B2 | 3/2012 | Olstad et al. |
| 8,137,281 B2 | 3/2012 | Huang et al. |
| 8,147,408 B2 | 4/2012 | Bunce et al. |
| 8,152,724 B2 | 4/2012 | Ridley et al. |
| 8,167,805 B2 | 5/2012 | Emery et al. |
| 8,216,149 B2 | 7/2012 | Oonuki et al. |
| 8,221,322 B2 | 7/2012 | Wang et al. |
| 8,228,028 B2 | 7/2012 | Schneider |
| 8,257,264 B2 | 9/2012 | Park et al. |
| 8,296,797 B2 | 10/2012 | Olstad et al. |
| 8,340,379 B2 | 12/2012 | Razzaque et al. |
| 8,350,902 B2 | 1/2013 | Razzaque et al. |
| 8,482,606 B2 | 7/2013 | Razzaque et al. |
| 8,554,307 B2 | 10/2013 | Razzaque et al. |
| 8,585,598 B2 | 11/2013 | Razzaque et al. |
| 8,641,621 B2 | 2/2014 | Razzaque et al. |
| 8,670,816 B2 | 3/2014 | Green et al. |
| 8,690,776 B2 | 4/2014 | Razzaque et al. |
| 8,831,310 B2 | 9/2014 | Razzaque et al. |
| 8,977,339 B1 | 3/2015 | Wu et al. |
| 9,107,698 B2 | 8/2015 | Razzaque et al. |
| 9,265,572 B2 | 2/2016 | Fuchs et al. |
| 9,282,947 B2 | 3/2016 | Razzaque et al. |
| 9,364,294 B2 | 6/2016 | Razzaque et al. |
| 9,398,936 B2 | 7/2016 | Razzaque et al. |
| 9,659,345 B2 | 5/2017 | Razzaque et al. |
| 9,675,319 B1 | 6/2017 | Razzaque et al. |
| 9,901,406 B2 | 2/2018 | State et al. |
| 9,949,700 B2 | 4/2018 | Razzaque et al. |
| 10,026,191 B2 | 7/2018 | Accomando et al. |
| 10,127,629 B2 | 11/2018 | Razzaque et al. |
| 10,136,951 B2 | 11/2018 | Razzaque et al. |
| 10,188,467 B2 | 1/2019 | Razzaque et al. |
| 10,278,778 B2 | 5/2019 | State et al. |
| 10,314,559 B2 | 6/2019 | Razzaque et al. |
| 10,398,513 B2 | 9/2019 | Razzaque et al. |
| 10,433,814 B2 | 10/2019 | Razzaque et al. |
| 10,733,700 B2 | 8/2020 | Keller et al. |
| 10,772,686 B2 | 9/2020 | State et al. |
| 10,820,944 B2 | 11/2020 | State et al. |
| 10,820,946 B2 | 11/2020 | Heaney et al. |
| 11,103,200 B2 | 8/2021 | Kohli et al. |
| 11,179,136 B2 | 11/2021 | Kohli et al. |

(56) References Cited

U.S. PATENT DOCUMENTS

| | | |
|---|---|---|
| 11,259,879 B2 | 2/2022 | Kohli et al. |
| 11,369,439 B2 | 6/2022 | State et al. |
| 11,464,575 B2 | 10/2022 | Heaney et al. |
| 11,464,578 B2 | 10/2022 | State et al. |
| 11,481,868 B2 | 10/2022 | Keller et al. |
| 11,484,365 B2 | 11/2022 | Kohli et al. |
| 11,534,245 B2 | 12/2022 | Heaney et al. |
| 11,684,429 B2 | 6/2023 | State et al. |
| 11,931,117 B2 | 3/2024 | Heaney et al. |
| 2001/0007919 A1 | 7/2001 | Shahidi |
| 2001/0016804 A1 | 8/2001 | Cunningham et al. |
| 2001/0031920 A1 | 10/2001 | Kaufman et al. |
| 2001/0041838 A1 | 11/2001 | Holupka et al. |
| 2001/0045979 A1 | 11/2001 | Matsumoto et al. |
| 2002/0010384 A1 | 1/2002 | Shahidi et al. |
| 2002/0032772 A1 | 3/2002 | Olstad et al. |
| 2002/0049375 A1 | 4/2002 | Strommer et al. |
| 2002/0077540 A1 | 6/2002 | Kienzle, III |
| 2002/0077543 A1 | 6/2002 | Grzeszczuk et al. |
| 2002/0103431 A1 | 8/2002 | Toker et al. |
| 2002/0105484 A1 | 8/2002 | Navab et al. |
| 2002/0135673 A1 | 9/2002 | Favalora et al. |
| 2002/0138008 A1 | 9/2002 | Tsujita et al. |
| 2002/0140814 A1 | 10/2002 | Cohen-Solal et al. |
| 2002/0156375 A1 | 10/2002 | Kessmam et al. |
| 2002/0198451 A1 | 12/2002 | Carson |
| 2003/0032878 A1 | 2/2003 | Shahidi |
| 2003/0040743 A1 | 2/2003 | Cosman et al. |
| 2003/0056799 A1 | 3/2003 | Young et al. |
| 2003/0073901 A1 | 4/2003 | Simon et al. |
| 2003/0135119 A1 | 7/2003 | Lee et al. |
| 2003/0163142 A1 | 8/2003 | Paltieli et al. |
| 2003/0164172 A1 | 9/2003 | Chumas et al. |
| 2003/0231789 A1 | 12/2003 | Willis et al. |
| 2003/0233123 A1 | 12/2003 | Kindlein et al. |
| 2004/0034313 A1 | 2/2004 | Leitner |
| 2004/0078036 A1 | 4/2004 | Keidar |
| 2004/0095507 A1 | 5/2004 | Bishop et al. |
| 2004/0116810 A1 | 6/2004 | Olstad |
| 2004/0147920 A1 | 7/2004 | Keidar |
| 2004/0152970 A1 | 8/2004 | Hunter et al. |
| 2004/0181144 A1 | 9/2004 | Cinquin et al. |
| 2004/0215071 A1 | 10/2004 | Frank et al. |
| 2004/0238732 A1 | 12/2004 | State et al. |
| 2004/0243146 A1 | 12/2004 | Chesbrough et al. |
| 2004/0243148 A1 | 12/2004 | Wasielewski |
| 2004/0249281 A1 | 12/2004 | Olstad |
| 2004/0249282 A1 | 12/2004 | Olstad |
| 2004/0254454 A1 | 12/2004 | Kockro |
| 2005/0010098 A1 | 1/2005 | Frigstad et al. |
| 2005/0033160 A1 | 2/2005 | Yamagata et al. |
| 2005/0085717 A1 | 4/2005 | Shahidi |
| 2005/0085718 A1 | 4/2005 | Shahidi |
| 2005/0090733 A1 | 4/2005 | Van Der Lugt et al. |
| 2005/0090742 A1 | 4/2005 | Mine et al. |
| 2005/0107679 A1 | 5/2005 | Geiger et al. |
| 2005/0111733 A1 | 5/2005 | Fors et al. |
| 2005/0159641 A1 | 7/2005 | Kanai |
| 2005/0182316 A1 | 8/2005 | Burdette et al. |
| 2005/0192564 A1 | 9/2005 | Cosman et al. |
| 2005/0219552 A1 | 10/2005 | Ackerman et al. |
| 2005/0222574 A1 | 10/2005 | Giordano et al. |
| 2005/0231532 A1 | 10/2005 | Suzuki et al. |
| 2005/0240094 A1 | 10/2005 | Pichon et al. |
| 2005/0251148 A1 | 11/2005 | Friedrich |
| 2006/0004275 A1 | 1/2006 | Vija et al. |
| 2006/0020204 A1 | 1/2006 | Serra et al. |
| 2006/0036162 A1 | 2/2006 | Shahidi et al. |
| 2006/0052792 A1 | 3/2006 | Boettiger et al. |
| 2006/0058609 A1 | 3/2006 | Olstad |
| 2006/0058610 A1 | 3/2006 | Olstad |
| 2006/0058674 A1 | 3/2006 | Olstad |
| 2006/0058675 A1 | 3/2006 | Olstad |
| 2006/0100505 A1 | 5/2006 | Viswanathan |
| 2006/0122495 A1 | 6/2006 | Kienzle |
| 2006/0135866 A1 | 6/2006 | Namii et al. |
| 2006/0184040 A1 | 8/2006 | Keller et al. |
| 2006/0193504 A1 | 8/2006 | Salgo et al. |
| 2006/0229594 A1 | 10/2006 | Francischelli et al. |
| 2006/0235290 A1 | 10/2006 | Gabriel et al. |
| 2006/0235538 A1 | 10/2006 | Rochetin et al. |
| 2006/0241450 A1 | 10/2006 | Da Silva et al. |
| 2006/0253030 A1 | 11/2006 | Altmann et al. |
| 2006/0253032 A1 | 11/2006 | Altmann et al. |
| 2006/0271056 A1 | 11/2006 | Terrill-Grisoni et al. |
| 2006/0282023 A1 | 12/2006 | Leitner |
| 2006/0293643 A1 | 12/2006 | Wallace et al. |
| 2007/0002582 A1 | 1/2007 | Burwell et al. |
| 2007/0016035 A1 | 1/2007 | Hashimoto |
| 2007/0024617 A1 | 2/2007 | Poole |
| 2007/0032906 A1 | 2/2007 | Sutherland et al. |
| 2007/0073155 A1 | 3/2007 | Park et al. |
| 2007/0073455 A1 | 3/2007 | Oyobe et al. |
| 2007/0078346 A1 | 4/2007 | Park et al. |
| 2007/0167699 A1 | 7/2007 | Lathuiliere et al. |
| 2007/0167701 A1 | 7/2007 | Sherman |
| 2007/0167705 A1 | 7/2007 | Chiang et al. |
| 2007/0167771 A1 | 7/2007 | Olstad |
| 2007/0167801 A1 | 7/2007 | Webler et al. |
| 2007/0225553 A1 | 9/2007 | Shahidi |
| 2007/0239281 A1 | 10/2007 | Gotte et al. |
| 2007/0244488 A1 | 10/2007 | Metzger et al. |
| 2007/0255136 A1 | 11/2007 | Kristofferson et al. |
| 2007/0270718 A1 | 11/2007 | Rochetin et al. |
| 2007/0276234 A1 | 11/2007 | Shahidi |
| 2007/0291000 A1 | 12/2007 | Liang et al. |
| 2008/0004481 A1 | 1/2008 | Bax et al. |
| 2008/0004516 A1 | 1/2008 | DiSilvestro et al. |
| 2008/0007720 A1 | 1/2008 | Mittal |
| 2008/0039723 A1 | 2/2008 | Suri et al. |
| 2008/0051910 A1 | 2/2008 | Kammerzell et al. |
| 2008/0091106 A1 | 4/2008 | Kim et al. |
| 2008/0114235 A1 | 5/2008 | Unal et al. |
| 2008/0146939 A1 | 6/2008 | McMorrow et al. |
| 2008/0161824 A1 | 7/2008 | McMillen |
| 2008/0183080 A1 | 7/2008 | Abraham |
| 2008/0200794 A1 | 8/2008 | Teichman et al. |
| 2008/0208031 A1 | 8/2008 | Kurpad et al. |
| 2008/0208081 A1 | 8/2008 | Murphy et al. |
| 2008/0214932 A1 | 9/2008 | Mollard et al. |
| 2008/0232679 A1 | 9/2008 | Hahn et al. |
| 2008/0287794 A1 | 11/2008 | Li et al. |
| 2008/0287805 A1 | 11/2008 | Li |
| 2008/0287837 A1 | 11/2008 | Makin et al. |
| 2009/0024030 A1 | 1/2009 | Lachaine et al. |
| 2009/0036902 A1 | 2/2009 | DeMaio et al. |
| 2009/0105597 A1 | 4/2009 | Abraham |
| 2009/0118613 A1 | 5/2009 | Krugman et al. |
| 2009/0118724 A1 | 5/2009 | Zvuloni et al. |
| 2009/0118727 A1 | 5/2009 | Pearson et al. |
| 2009/0131783 A1 | 5/2009 | Jenkins et al. |
| 2009/0137907 A1 | 5/2009 | Takimoto et al. |
| 2009/0148008 A1 | 6/2009 | Wiemker et al. |
| 2009/0196480 A1 | 8/2009 | Nields et al. |
| 2009/0234369 A1 | 9/2009 | Bax et al. |
| 2009/0312629 A1 | 12/2009 | Razzaque et al. |
| 2010/0041949 A1 | 2/2010 | Tolkowsky |
| 2010/0045783 A1 | 2/2010 | State et al. |
| 2010/0152570 A1 | 6/2010 | Navab |
| 2010/0185087 A1 | 7/2010 | Nields et al. |
| 2010/0198402 A1 | 8/2010 | Greer et al. |
| 2010/0208963 A1 | 8/2010 | Kruecker et al. |
| 2010/0268072 A1 | 10/2010 | Hall et al. |
| 2010/0268085 A1 | 10/2010 | Kruecker et al. |
| 2010/0296718 A1 | 11/2010 | Ostrovsky-Berman et al. |
| 2010/0298705 A1 | 11/2010 | Pelissier et al. |
| 2010/0305448 A1 | 12/2010 | Dagonnau et al. |
| 2010/0312121 A1 | 12/2010 | Guan |
| 2010/0331252 A1 | 12/2010 | Hamrick |
| 2011/0043612 A1 | 2/2011 | Keller et al. |
| 2011/0046483 A1 | 2/2011 | Fuchs et al. |
| 2011/0051083 A1 | 3/2011 | Geggel |
| 2011/0057930 A1 | 3/2011 | Keller et al. |
| 2011/0082351 A1 | 4/2011 | Razzaque et al. |

(56) References Cited

U.S. PATENT DOCUMENTS

| | | |
|---|---|---|
| 2011/0137156 A1 | 6/2011 | Razzaque et al. |
| 2011/0201915 A1 | 8/2011 | Gogin et al. |
| 2011/0201976 A1 | 8/2011 | Sanghvi et al. |
| 2011/0208055 A1 | 8/2011 | Dalal et al. |
| 2011/0230351 A1 | 9/2011 | Fischer et al. |
| 2011/0237947 A1 | 9/2011 | Boctor et al. |
| 2011/0238043 A1 | 9/2011 | Kleven |
| 2011/0274324 A1 | 11/2011 | Clements et al. |
| 2011/0282188 A1 | 11/2011 | Burnside et al. |
| 2011/0288412 A1 | 11/2011 | Deckman et al. |
| 2011/0295108 A1 | 12/2011 | Cox et al. |
| 2011/0301451 A1 | 12/2011 | Rohling |
| 2012/0035473 A1 | 2/2012 | Sanghvi et al. |
| 2012/0059260 A1 | 3/2012 | Robinson |
| 2012/0071759 A1 | 3/2012 | Hagy et al. |
| 2012/0078094 A1 | 3/2012 | Nishina et al. |
| 2012/0138658 A1 | 6/2012 | Ullrich et al. |
| 2012/0143029 A1 | 6/2012 | Silverstein et al. |
| 2012/0143055 A1 | 6/2012 | Ng et al. |
| 2012/0165679 A1 | 6/2012 | Orome et al. |
| 2012/0215096 A1 | 8/2012 | Gilboa |
| 2012/0230559 A1 | 9/2012 | Itai |
| 2012/0237105 A1 | 9/2012 | Mielekamp |
| 2012/0238857 A1 | 9/2012 | Wong et al. |
| 2012/0259210 A1 | 10/2012 | Harhen et al. |
| 2013/0030286 A1 | 1/2013 | Alouani et al. |
| 2013/0044930 A1 | 2/2013 | Li et al. |
| 2013/0079770 A1 | 3/2013 | Kyle, Jr. et al. |
| 2013/0090646 A1 | 4/2013 | Moss et al. |
| 2013/0096497 A1 | 4/2013 | Duindam et al. |
| 2013/0132374 A1 | 5/2013 | Olstad et al. |
| 2013/0144165 A1 | 6/2013 | Ebbini et al. |
| 2013/0151533 A1 | 6/2013 | Udupa et al. |
| 2013/0178745 A1 | 7/2013 | Kyle et al. |
| 2013/0197357 A1 | 8/2013 | Green et al. |
| 2013/0218024 A1 | 8/2013 | Boctor et al. |
| 2013/0249787 A1 | 9/2013 | Morimoto |
| 2014/0051987 A1 | 2/2014 | Kowshik et al. |
| 2014/0058387 A1 | 2/2014 | Kruecker et al. |
| 2014/0078138 A1 | 3/2014 | Martin et al. |
| 2014/0180074 A1 | 6/2014 | Green |
| 2014/0201669 A1 | 7/2014 | Liu et al. |
| 2014/0275760 A1 | 9/2014 | Lee et al. |
| 2014/0275810 A1 | 9/2014 | Keller et al. |
| 2014/0275997 A1 | 9/2014 | Chopra et al. |
| 2014/0350390 A1 | 11/2014 | Kudavelly et al. |
| 2015/0235373 A1 | 8/2015 | Kato et al. |
| 2015/0238259 A1 | 8/2015 | Albeck et al. |
| 2015/0257847 A1 | 9/2015 | Higgins et al. |
| 2016/0117857 A1 | 4/2016 | State et al. |
| 2016/0166334 A1 | 6/2016 | Razzaque et al. |
| 2016/0196694 A1 | 7/2016 | Lindeman |
| 2016/0228068 A1 | 8/2016 | Hancu et al. |
| 2016/0270862 A1 | 9/2016 | Fuchs et al. |
| 2016/0354152 A1 | 12/2016 | Beck |
| 2017/0024903 A1 | 1/2017 | Razzaque et al. |
| 2017/0099479 A1 | 4/2017 | Browd et al. |
| 2017/0325896 A1 | 11/2017 | Donhowe et al. |
| 2017/0340266 A1 | 11/2017 | Gardner et al. |
| 2017/0348067 A1 | 12/2017 | Krimsky |
| 2018/0289344 A1 | 10/2018 | Green et al. |
| 2020/0046315 A1 | 2/2020 | State et al. |
| 2021/0113273 A1 | 4/2021 | State et al. |
| 2022/0192611 A1 | 6/2022 | Kohli et al. |
| 2022/0296208 A1 | 9/2022 | Kohli et al. |
| 2023/0200916 A1 | 6/2023 | Heaney et al. |
| 2023/0222624 A1 | 7/2023 | Keller et al. |
| 2023/0233264 A1 | 7/2023 | State et al. |

FOREIGN PATENT DOCUMENTS

| | | |
|---|---|---|
| JP | H07-116164 A | 5/1995 |
| WO | WO 96/005768 | 2/1996 |
| WO | WO 97/015249 | 5/1997 |
| WO | WO 97/017014 | 5/1997 |
| WO | WO 97/029682 | 8/1997 |
| WO | WO 01/039683 | 6/2001 |

OTHER PUBLICATIONS

U.S. Appl. No. 15/068,323 including without limitation Office Actions, Amendments, Remarks, and any other potentially relevant documents, filed Mar. 11, 2016, Razzaque et al.

U.S. Appl. No. 17/652,785 including its ongoing prosecution history, including without limitation Office Actions, Amendments, Remarks, and any other potentially relevant documents, filed Feb. 28, 2022, Kohli et al.

U.S. Appl. No. 17/664,797 including without limitation Office Actions, Amendments, Remarks, and any other potentially relevant documents, filed May 24, 2022, State et al.

U.S. Appl. No. 18/051,399 including its ongoing prosecution history, including without limitation Office Actions, Amendments, Remarks, and any other potentially relevant documents, filed Oct. 31, 2022, Kohli et al.

"3D Laparoscope Technology," http://www.inneroptic.com/tech_3DL.htm, copyright 2007 InnerOptic Technology, Inc. printed Sep. 19, 2007, 2 pages.

"AIM 3D Needle Placement Software from InnerOptic", Medgadget, Sep. 21, 2012.

AIM Section 5: 510k Summary, submitted by InnerOptic Technology, Inc., in 5 pages, submission date May 17, 2012.

"Cancer Facts & Figures 2004," www.cancer.org/downloads/STT/CAFF_finalPWSecured.pdf, copyright 2004 American Cancer Society, Inc., printed Sep. 19, 2007, 60 pages.

Cancer Prevention & Early Detection Facts & Figures 2004; National Center for Tobacco-Free Kids; 2004; American Cancer Society; USA.

"David Laserscanner <—Latest News <—Institute for Robotics and Process Control <—Te . . . ," http://www/rob.cs.tu-bs.de/en/news/david, printed Sep. 19, 2007, 1 page.

"InnerOptic's AIM System Receives DA 510(K) Clearance", InnerOptic Technology, Inc., Sep. 18, 2012.

"Laser scanned 3d model Final" video, still image of video attached, http://www.youtube.com/watch?v+DaLglgmoUf8, copyright 2007 YouTube, LLC, printed Sep. 19, 2007, 2 pages.

"Olympus Endoscopic Ultrasound System," www.olympusamerica.com/msg_section/download_brochures/135_b_gfum130.pdf, printed Sep. 20, 2007, 20 pages.

"Point Grey Research Inc.—Imaging Products—Triclops SDK Samples," http://www.ptgrey.com/products/triclopsSDK/samples.asp, copyright 2007 Point Grey Research Inc., printed Sep. 19, 2007, 1 page.

"Robbins, Mike—Computer Vision Research—Stereo Depth Perception," http://www.compumike.com/vision/stereodepth.php, copyright 2007 Michael F. Robbins, printed Sep. 19, 2007, 3 pages.

"RUE, Registered Ultrasound-Endoscope," copyright 2007 InnerOptic Technology, Inc., 2 pages.

Advertisement, "Inspeck 3DC 3D Capturor," Inspeck 3DC 3D Capturor (www.inspeck.com), 1998.

Advertisement, "Virtual 3D High Speed Non-Contact Surface Perception," Virtual 3-D Technologies Corporation (www.virtual3dtech.com)., Dec. 21, 1998.

Advertisements, "Virtuoso," Visual Interface, Inc. (www.visint.com), Dec. 21, 1998.

Akka, "Automatic Software Control of Display Parameters for Stereoscopic Graphics Images," SPIE vol. 1669: Stereoscopic Displays and Applications III, pp. 31-38 (1992).

Ali et al., "Near Infrared Spectroscopy and Imaging to Probe Differences in Water Content in Normal and Cancer Human Prostate Tissues," Technology in Cancer Research & Treatment; Oct. 2004; 3(5):491-497; Adenine Press.

Aylward et al., Analysis of the Parameter Space of a Metric for Registering 3D Vascular Images, in W. Niessen and M. Viergever (Eds.): MICCAI 2001, LNCS 2208, pp. 932-939, 2001.

Aylward et al., Registration and Analysis of Vascular Images, International Journal of Computer Vision 55(2/3), 123-138, 2003.

(56) References Cited

OTHER PUBLICATIONS

Aylward, et al., Intra-Operative 3D Ultrasound Augmentation, Proceedings of the IEEE International Symposium on Biomedical Imaging, Washington, Jul. 2002.
Azuma et al., "Improving Static and Dynamic Registration in an Optical See-Through HMD," Paper Presented at SIGGRAPH '94 Annual Conference in Orlando, FL, 197-204; (1994).
Azuma, "A Survey of Augmented Reality," Presence: Teleoperators and Virtual Environments 6, 4:1-48 (Aug. 1997).
Badler et al., "Simulating Humans: Computer Graphics, Animation, and Control," Oxford University Press (1993).
Bajura, Michael et al., "Merging Virtual Objects with the Real World: Seeing Ultrasound Imagery within the Patient," Computer Graphics, Proceedings of SIGGRAPH 1992, vol. 26(2), pp. 203-210, available from www.cs.unc.edu/~fuchs/publications/MergVirtObjs92.pdf, printed Sep. 20, 2007, 8 pages.
Benavides et al., "Multispectral digital colposcopy for in vivo detection of cervical cancer," Optics Express; May 19, 2003; 11(10) Optical Society of America; USA.
Beraldin, J.A. et al., "Optimized Position Sensors for Flying-Spot Active Triangulation Systems," Proceedings of the Fourth International Conference on a 3-D Digital Imaging and Modeling (3DIM), Banff, Alberta, Canada, Oct. 6-10, 2003, pp. 334-341, NRC 47083, copyright 2003 National Research Council of Canada, http://iit-iti.nrc-cnrc.gc.ca/iit-publications-iti/docs/NRC-47083.pdf, printed Sep. 19, 2007, 9 pages.
Billinghurst, M. et al., Research Directions in Handheld AR; Int. J. of Virtual Reality 5(2),51-58 (2006).
Blais, F., "Review of 20 Years of Range Sensor Development," Journal of Electronic Imaging, 13(1): 231-240, Jan. 2004, NRC 46531, copyright 2004 National Research Council of Canada, http://iit-iti.nrc-cnrc.gc.ca/iit-publications-iti/docs/NRC-46531.pdf, printed Sep. 19, 2007, 14 pages.
Bouguet, Jean-Yves, "Camera Calibration Toolbox for Matlab," www.vision.caltech.edu/bouguetj/calib_doc, printed Sep. 20, 2007, 5 pages.
Buxton et al.; "Colposcopically directed punch biopsy: a potentially misleading investigation," British Journal of Obstetrics and Gynecology; Dec. 1991; 98:1273-1276.
Caines, Judy S. et al. Stereotaxic Needle Core Biopsy of Breast Lesions Using a Regular Mammographic Table with an Adaptable Stereotaxic Device, American Journal of Roentgenology, vol. 163, No. 2, Aug. 1994, pp. 317-321. Downloaded from www.ajrorline.org on Jul. 10, 2013.
Cantor et al., "Cost-Effectiveness Analysis of Diagnosis and Management of Cervical Squamous Intraepithelial Lesions," Diagnostic Strategies for SILs; Feb. 1998; 91(2):270-277.
Catalano et al. "Multiphase helical CT findings after percutaneous ablation procedures for hepatocellular carcinoma." Abdom. Imaging, 25(6),2000, pp. 607-614.
Chiriboga et al., "Infrared Spectroscopy of Human Tissue. IV. Detection of Dysplastic and Neoplastic Changes of Human Cervical Tissue Via Infrared Microscopy," Cellular and Molecular Biology; 1998; 44(1): 219-229.
Crawford, David E. et al., "Computer Modeling of Prostate Biopsy: Tumor Size and Location—Not Clinical Significance—Determine Cancer Detection," Journal of Urology, Apr. 1998, vol. 159(4), pp. 1260-1264, 5 pages.
Deering, Michael "High Resolution Virtual Reality." Proceedings of SIGGRAPH '92, Computer Graphics, 26(2), 1992, pp. 195-202.
Depiero et al., "3-D Computer Vision Using Structured Light: Design, Calibration and Implementation Issues," The University of Tennessee, pp. 1-46, (1996).
Dodd, G.D. et al. "Minimally invasive treatment of malignant hepatic tumors: at the threshold of a major breakthrough." Radiographies 20(1),2000, pp. 9-27.
Drascic et al., "Perceptual Issues in Augmented Reality," SPIE vol. 2653: Stereoscopic Displays and Virtual Reality Systems III, pp. 123-134 (Feb. 1996).
Dumoulin, C.L. et al, Real-Time Position Monitoring of Invasive Devices Using Magnetic Resonance, Magnetic Resonance in Medicine, vol. 29, Issue 3, Mar. 1993, pp. 411-415.
Edwards et al., Video See-Through Design for Merging of Real and Virtual Environments, VRAIS '93, pp. 1-11 (1993).
Fahey et al., "Meta-analysis of Pap Test Accuracy; American Journal of Epidemiology," 1995 141(7):680-689; The John Hopkins University School of Hvqiene and Public Health; USA.
Foxlin et al., "An Inertial Head-Orientation Tracker with Automatic Drift Compensation for Use with HMD's," Proceedings of the 1994 Virtual Reality Software and Technology Conference, Aug. 23-26, 1994, Singapore, pp. 159-173 (1994).
Fronheiser et al., Real-Time 3D Color Doppler for Guidance of Vibrating Interventional Devices, IEEE Ultrasonics Symposium, pp. 149-152 (2004).
Fuchs, Henry et al. "Augmented Reality Visualization for Laparoscopic Surgery," Proceedings of Medical Image Computing and Computer-Assisted Intervention (MICCAI) 1998, pp. 934-943, available from www.cs.unc.edu/~fuchs/publications /AugRealVis_LaparoSurg98.pdf, printed Sep. 20, 2007, 10 pages.
Fuchs, et al.: "Optimizing a Head-Tracked Stereo Display System to Guide Hepatic Tumor Ablation," Departments of Computer Sciences and Radiology, and School of Medicine, University of North Carolina at Chapel Hill; InnerOptic Technology, Inc. 2008.
Fuchs, et al.: "Virtual Environments Technology To Aid Needle Biopsies of the Breast," Health Care in the Information Age, Ch. 6, pp. 60-61, Presented in San Diego, Jan. 17-20, 1996, published by IOS Press and Ohmsha Feb. 1996.
Fuhrmann et al, Comprehensive calibration and registration procedures for augmented reality; Proc. Eurographics Workshop on Virtual Environments 2001, 219-228 (2001).
Garrett, William F. et al., "Real-Time Incremental Visualization of Dynamic Ultrasound Volumes Using Parallel BSP Trees,"Proceedings of IEEE Visualization 1996, pp. 235-240, available from www.cs.unc.edu/~andrei/pubs/1996_VIS_dualBSP_Mac.pdf, printed Sep. 20, 2007, 7 pages.
Georgakoudi et al., "Trimodal spectroscopy for the detection and characterization of cervical precancers in vivo," American Journal of Obstetrics and Gynecology; Mar. 2002; 186(3):374-382; USA.
StereoMirror Technology Webpage, http://www.planar.com/products/flatpanel_monitors/stereoscopic/ (Printed Dec. 29, 2011).
Herline et al., Surface Registration for Use in Interactive, Image-Guided Liver Surgery, Computer Aided Surgery 5:11-17 (2000).
Holloway, R.; Registration Error Analysis for Augmented Reality; Presence: Teleoperators and Virtual Environments 6(4), 413-432 (1997).
Hornung et al., "Quantitative near-infrared spectroscopy of cervical dysplasia in vivo," Human Reproduction; 1999; 14(11):2908-2916; European Society of Human Reproduction and Embryology.
Howard, M.D., et al.: "An Electronic Device for Needle Placement during Sonographically Guided Percutaneous Intervention", Radiology 2001; 218:905-911.
InnerAim Brochure; 3D Visualization Software for Simpler, Safer, more Precise Aiming, Published no earlier than Apr. 1, 2010.
InVision System Brochure; A "GPS" for Real-Time 3D Needle Visualization & Guidance, Published no earlier than Mar. 1, 2008.
Jacobs, Marco C. et al., "Managing Latency in Complex Augmented Reality Systems," ACM SIGGRAPH Proceedings of the Symposium of Interactive 3D Graphics 1997, pp. 49-54, available from www.cs.unc.edu/~us/Latency//ManagingRelativeLatency.html, printed Sep. 20, 2007, 12 pages.
Jolesz, Ferenc A, M.D., et al. MRI-Guided Laser-Induced Interstitial Thermotherapy: Basic Principles, SPIE Institute on Laser-Induced Interstitial Thermotherapy (L1TT), Jun. 22-23, 1995, Berlin, Germany.
Kadi, A Majeed, et al., Design and Simulation of an Articulated Surgical Arm for Guiding Sterotactic Neurosurgery, SPIE vol. 1708 Applications of Artificial Intelligence X: Machine Vision and Robotics (1992). Downloaded from: http://proceedings.spiedigitallibrary.org/ on Jul. 11, 2013.
Kanbara et al., "A Stereoscopic Video See-through Augmented Reality System Based on Real-time Vision-Based Registration," Nara Institute of Science and Technology, pp. 1-8 (2000).

(56) References Cited

OTHER PUBLICATIONS

Kato, Amami, et al., A frameless, armless navigational system for computer-assisted neurosurgery, Journal of Neurosurgery, vol. 74, No. 5, May 1991, pp. 845-849.
Keller et al., "What is it in Head Mounted Displays (MDs) that really make them all so terrible?," pp. 1-8 (1998).
Lass, Amir, "Assessment of Ovarian Reserve," Human Reproduction, 2004, vol. 19(3), pp. 467-469, available from http://humrep.oxfordjournals.orgcgi/reprint/19/3/467, printed Sep. 20, 2007, 3 pages.
Lee, et al., "Modeling Real Objects Using Video See-Through Augmented Reality," Proceedings of the Second International Symposium on Mixed Reality, ISMR 2001, pp. 19-26 (Mar. 14-15, 2001).
Lee et al., "Modeling Real Objects Using Video See-Through Augmented Reality," Presence, 11(2):144-157 (Apr. 2002).
Leven et al., DaVinci Canvas: A Telerobotic Surgical System with Integrated, Robot-Assisted, Laparoscopic Ultrasound Capability, in J. Duncan and G. Gerig (Eds.): MICCAI 2005, LNCS 3749, pp. 811-818, 2005.
Levy, et al., An Internet-Connected, Patient Specific, Deformable Brain Atlas Integrated into a Surgical Navigation System, Journal of Digital Imaging, vol. 10, No. 3. Suppl. 1 (August), 1997: pp. 231-237.
Lindeman, A Low-Cost, Low-latency Approach to Dynamic Immersion in Occlusive Head-Mounted Displays, University of Canterbury, WPI,—Poster from IEEE VR 2016, Mar. 19-23, 2016.
Lipton, "Foundations of the Steroscopic Cinema A Study in Depth," Van Nostrad Reinhold Company, pp. 1-319 (1982).
Livingston, Mark A. et al., "Magnetic Tracker Calibration for Improved Augmented Reality Registration," Presence: Teleoperators and Virtual Environments, 1997, vol. 6(5), pp. 532-546, available from www.cs.unc.edu/~andrei/pubs/1997_Presence_calibr.pdf, printed Sep. 20, 2007, 14 pages.
Matsunaga et al., "The Effect of the Ratio Difference of Overlapped Areas of Stereoscopic Images on each Eye in a Teleoperalion," Stereoscopic Displays and Virtual Reality Systems VII, Proceedings of SPIE, 3957:236-243 (2000).
Meehan, Michael et al., "Effect of Latency on Presence in Stressful Virtual Environment," Proceedings of IEEE Virtual Reality 2003, pp. 141-148, available from http://www.cs.unc.edu/~eve/pubs.html, printed Sep. 20, 2007, 8 pages.
Milgram et al., "Adaptation Effects in Stereo due to Online Changes in Camera Configuration," SPIE vol. 1669-13, Stereoscopic Displays and Applications III, 17 pages (1992).
Mitchell et al., "Colposcopy for the Diagnosis of Squamous Intraepithelial lesions: A metaanalysis," Obstetrics and Gynecology; Apr. 1998; 91(4):626-631.
Nakamoto et al., 3D Ultrasound System Using a Magneto-optic Hybrid Tracker for Augmented Reality Visualization in Laparoscopic Liver Surgery, in T. Dohi and R. Kikinis (Eds.): MICCAI 2002, LNCS 2489, pp. 148-155, 2002.
Nordstrom et al., "Identification of Cervical Intraepithelial Neoplasia (CIN) Using UV-Excited Fluorescence and Diffuse-Reflectance Tissue Spectroscopy," Lasers in Surgery and Medicine; 2001; 29; pp. 118-127; Wiley-Liss, Inc.
Ohbuchi et al. "An Incremental Volume Rendering Algorithm for Interactive 3D Ultrasound Imaging", UNC-CH Computer Science Technical Report TR91-003, (1991).
Ohbuchi et al., "Incremental Volume Reconstruction and Rendering for 3D Ultrasound Imaging," Visualization in Biomedical Computing, SPIE Proceedings, pp. 312-323, (Oct. 13, 1992).
Ohbuchi, "Incremental Acquisition and Visualization of 3D Ultrasound Images," Ph.D. Dissertation, UNC-CH Computer Science Technical Report TR95-023, (1993).
Ohnesorge Lauren K., "InnerOptic technology wins FDA approval", Triangle Business Journal, Sep. 19, 2012.
Pogue, Brian W. et al., "Analysis of acetic acid-induced whitening of high-grade squamous intraepitheliallesions," Journal of Biomedical Optics; Oct. 2001; 6(4):397-403.
Press Release: Pathfinder and InnerOptic Announce Technology Integration to Enhance Visualization and Outcomes in Liver Surgery, Published Mar. 6, 2013.
Raij, A.B., et al., Comparing Interpersonal Interactions with a Virtual Human to Those with a Real Human; IEEE Transactions on Visualization and Computer Graphics 13(3), 443-457 (2007).
Raz et al, Real-Time Magnetic Resonance Imaging-Guided Focal Laser Therapy in Patients with Low-Risk Prostate Cancer, European Urology 58, pp. 173-177. Mar. 12, 2010.
Rieder, et al., "GPU-Based Real-Time Approximation of The Ablation Zone for Radiofrequency Ablatin," IEEE Transactions on Visualization and Computer Graphics 17.12 (2011): 1812-1821.
Robinett et al., "A Computational Model for the Stereoscopic Optics of a Head-Mounted Display," SPIE vol. 1457, Stereoscopic Displays and Applications II, pp. 140-160 (1991).
Rolland et al., Towards Quantifying Depth and Size Perception in Virtual Environments, Presence: Teleoperators and Virtual Environments, Winter 1995, vol. 4, Issue 1, pp. 1-21 and 24-49.
Rosenthal, Michael et al., "Augmented Reality Guidance for Needle Biopsies: An Initial Randomized, Controlled Trial in Phantoms," Proceedings of Medical Image Analysis, Sep. 2002, vol. 6(3), pp. 313-320, available from www.cs.unc.edu/~fuchs/publications/AugRealGuida_NeedleBiop02.pdf, printed Sep. 20, 2007, 8 pages.
Rosenthal, Michael et al., "Augmented Reality Guidance for Needle Biopsies: A Randomized, Controlled Trial in Phantoms," Proceedings of MICCAI 2001, eds. W. Niessen and M. Viergever, Lecture Notes in Computer Science, 2001, vol. 2208, pp. 240-248, available from www.cs.unc.edu/~us/AugmentedRealityAssistance.pdf, printed Sep. 20, 2007, 9 pages.
Screenshots from video produced by the University of North Carolina, produced circa 1992.
"Sony Introduces Head-Mounted Display for Endoscopic Surgery" (Jul. 23, 2013), retrieved Sep. 27, 2016, 5 pages, available at http://www.medgaget.com/2013/07/sony-introduces-head-mounted-display-for-endoscopic-surgery.html.
"Sony Introduces 'head-mount image processing unit' for endoscopic image display" (Jul. 23, 2013), retrieved Sep. 27, 2016, 14 pages, available at http://www.sony.net/SonyInfo/News/Press/201307/13-085E/index.html.
State et al., "Case Study: Observing a Volume Rendered Fetus within a Pregnant Patient,"Proceedings of IEEE Visualization 1994, pp. 364-368, available from www.cs.unc.edu/~fuchs/publications/cs-ObservVolRendFetus94.pdf, printed Sep. 20, 2007, 5 pages.
State et al., "Interactive Volume Visualization on a Heterogeneous Message-Passing Multicomputer," Proceedings of 1995 Symposium on Interactive 3D Graphics, 1995, pp. 69-74, 208, available from www.cs.unc.edu/~andrei/pubs/1995_I3D_vol2_Mac.pdf, printed Sep. 20, 2007.
State et al., "Simulation-Based Design and Rapid Prototyping of a Parallax-Free, Orthoscopic Video See-Through Head-Mounted Display," Proceedings of International Symposium on Mixed and Augmented Reality (ISMAR) 2005, available from www.cs.unc.edu/~andrei/pubs/2005_ISMAR_VSTHMD_design.pdf, printed Sep. 20, 2007, 4 pages.
State et al., "Stereo Imagery from the UNC Augmented Reality System for Breast Biopsy Guidance" Proc. Medicine Meets Virtual Reality (MMVR) 2003 (Newport Beach, CA, Jan. 22-25, 2003).
State et al., "Superior Augmented Reality Registration by Integrating Landmark Tracking and Magnetic Tracking," ACM SIGGRAPH Computer Graphics, Proceedings of SIGGRAPH 1996, Annual Conference Series, 10 pages (Aug. 1996).
State et al., "Technologies for Augmented Reality Systems: Realizing Ultrasound-Guided Needle Biopsies," Proc. SIGGRAPH 96 (New Orleans, LA, Aug. 4-9, 1996). In Computer Graphics Proceedings, Annual Conference Series, 1996, ACM SIGGRAPH, pp. 439-446.
State, Andrei "Exact Eye Contact with Virtual Humans." Proc. IEEE International Workshop on Human Computer Interaction 2007 (Rio de Janeiro, Brazil, Oct. 20, 2007), pp. 138-145.
State, et al.: Contextually Enhanced 3D Visualization for Multi-Born Tumor Ablation Guidance, Departments of Computer Science

(56) References Cited

OTHER PUBLICATIONS and Radiology, and School of Medicine, University of North Carolina at Chapel Hill; InnerOptic Technology, Inc. 2008, Chapel Hill, NC, pp. 70-77.

Symons et al., "What are You Looking at? Acuity for Triadic Eye Gaze," J. Gen. Psychology 131(4), pp. 451-469 (2004).

Takacs et al., "The Virtual Human Interface: A Photorealistic Digital Human," IEEE Computer Graphics and Applications 23(5), pp. 38-45 (2003).

Takagi et al., "Development of a Stereo Video See-through HMD for AR Systems," IEEE, pp. 68-77 (2000).

Takayama et al., "Virtual Human with Regard to Physical Contact and Eye Contact," Entertaining Computing 2005, LNCS, vol. 3711, pp. 268-278 (2005).

Ultraguide 1000 System, Ultraguide, www.ultraguideinc.com, 1998.

Van Staveren et al., "Light Scattering in Intralipid-10% in the wavelength range of 400-1100 nm," Applied Optics; Nov. 1991; 30(31):4507-4514.

Viola et al., "Alignment by Maximization of Mutual Information," International Journal of Computer Vision, vol. 24, No. 2, pp. 137-154 (1997).

Viola, Paul A., Alignment by Maximization of Mutual Information, Ph.D. Dissertation, MIT-Artificial Intelligence Laboratory Technical Report No. 1548 (Jun. 1995), 156 pages.

Ware et al., "Dynamic Adjustment of Stereo Display Parameters," IEEE Transactions on Systems, Many and Cybernetics, 28(1):1-19 (1998).

Watson et al., "Using Texture Maps to Correct for Optical Distortion in Head-Mounted Displays," Proceedings of the Virtual Reality Annual Symposium '95, IEEE, pp. 1-7 (1995).

Welch, Hybrid Self-Tracker: An Inertial/Optical Hybrid Three-Dimensional Tracking System, University of North Carolina Chapel Hill Department of Computer Science, TR 95-048 (1995).

Yinghui et al., Real-Time Deformation Using Modal Analysis on Graphics Hardware, Graphite 2006, Kuala Lumpur, Malaysia, Nov. 29-Dec. 2, 2006.

Zitnick et al., "Multi-Base Stereo Using Surface Extraction," Visual Interface Inc., (Nov. 24, 1996).

U.S. Appl. No. 18/608,338 including its ongoing prosecution history, including without limitation Office Actions, Amendments, Remarks, and any other potentially relevant documents, filed Mar. 18, 2024, Heaney et al.

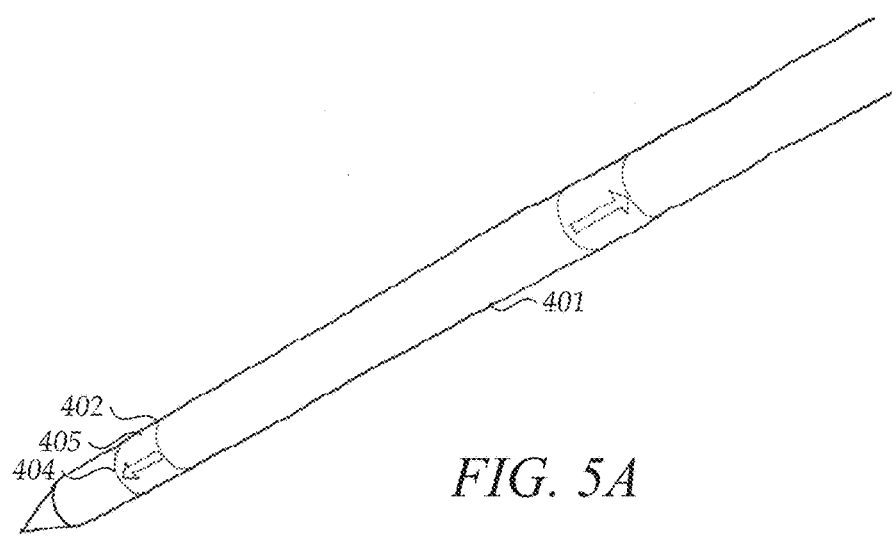
FIG. 5A
FIG. 5B
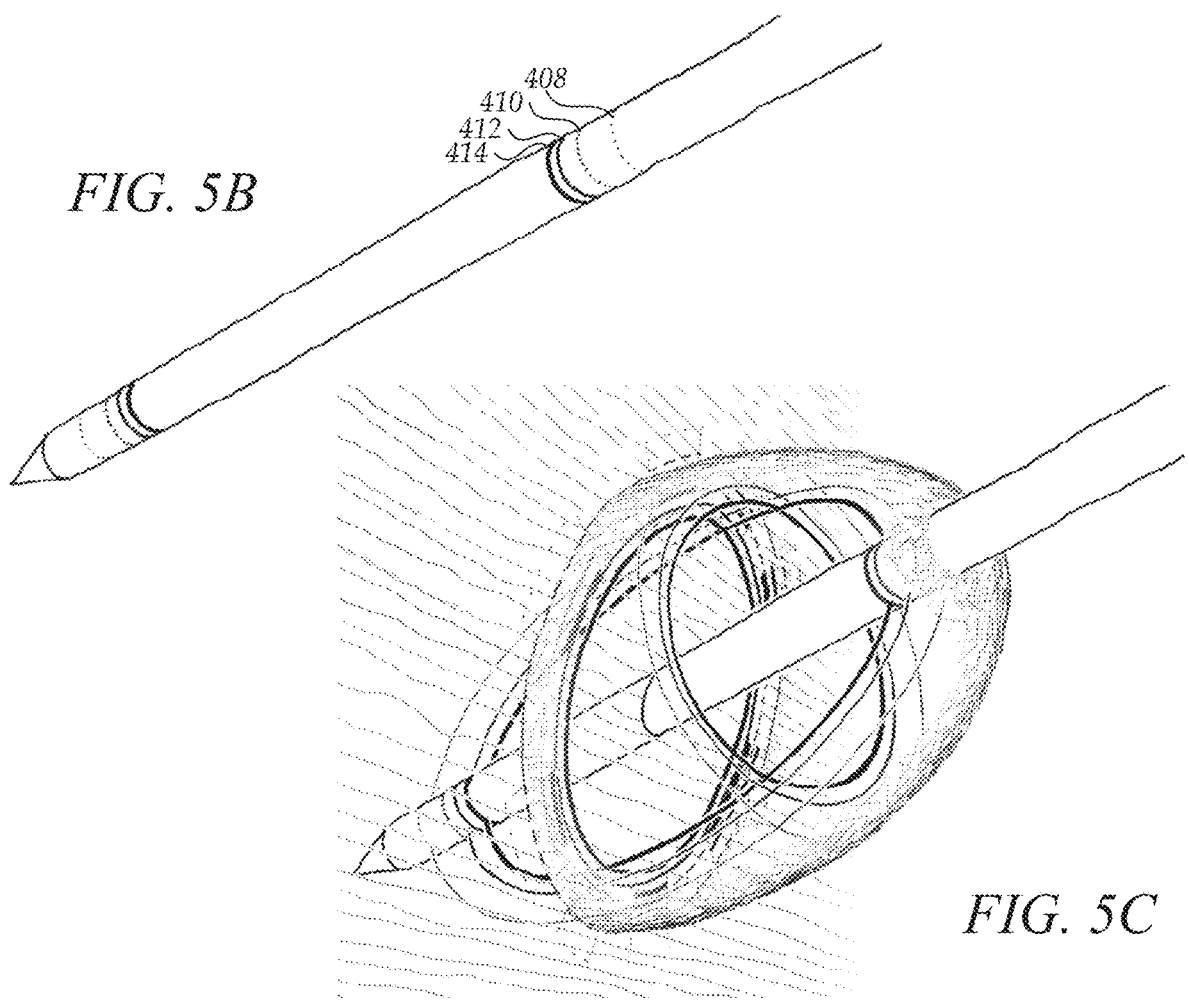
FIG. 5C

AFFECTED REGION DISPLAY ASSOCIATED WITH A MEDICAL DEVICE

CROSS-REFERENCE TO RELATED APPLICATIONS

The present application is a continuation of U.S. patent application Ser. No. 17/071,459, filed Oct. 15, 2020, entitled AFFECTED REGION DISPLAY ASSOCIATED WITH A MEDICAL DEVICE, which is a continuation of U.S. patent application Ser. No. 15/882,709, filed Jan. 29, 2018, entitled AFFECTED REGION DISPLAY BASED ON A VARIANCE PARAMETER ASSOCIATED WITH A MEDICAL DEVICE, which is a continuation of U.S. patent application Ser. No. 14/872,930, filed Oct. 1, 2015, entitled AFFECTED REGION DISPLAY ASSOCIATED WITH A MEDICAL DEVICE, which claims priority benefit to U.S. Provisional Application No. 62/059,077, filed Oct. 2, 2014, entitled ABLATION AREA VISUALIZATIONS, each of which is hereby incorporated herein by reference in its entirety. Any and all applications for which a foreign or domestic priority claim is identified in the Application Data Sheet as filed with the present application are incorporated by reference under 37 CFR 1.57 and made a part of this specification.

TECHNICAL FIELD

The systems and methods disclosed herein relate generally to computer systems facilitating medical device guidance through tissue by a medical practitioner.

BACKGROUND

Various medical device systems are available to aid a healthcare provider to guide a medical device in a patient. The medical device systems can provide various image guidance cues to aid the healthcare provider, and can also provide views of images of an imaged area and of virtual medical devices corresponding to physical medical devices.

BRIEF DESCRIPTION OF THE DRAWINGS

FIGS. 5A, 5B, and 5C are diagrams illustrating embodiments of displayed affected regions, including surface display regions.

DETAILED DESCRIPTION

Figure 1:
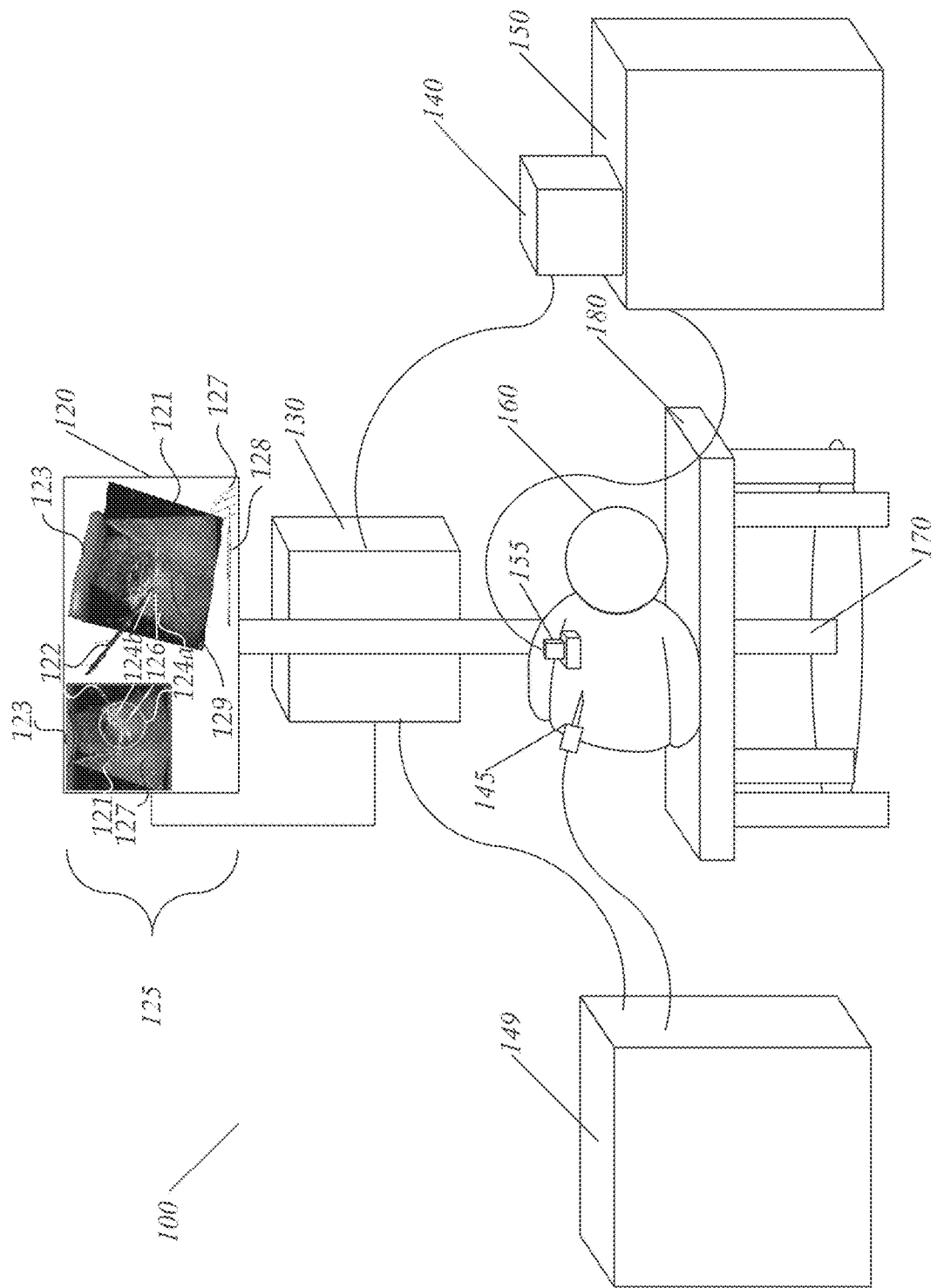
FIG. 1 is a diagram of an embodiment of a system for image-guided medical procedures.

Implementations disclosed herein provide systems, methods, and apparatus for generating images facilitating medical device insertion into tissue by an operator. Certain embodiments pertain to a free-hand medical device guidance system. The system can provide the healthcare provider manual control over the medical device, while making the spatial relationships between the target, medical device and U/S image more intuitive via a visual display. Using this visual feedback, the operator can adjust the medical device's position, orientation, or trajectory. Certain of the contemplated embodiments can be used in conjunction with systems described in greater detail in U.S. patent application Ser. No. 13/014,587, filed Jan. 26, 2011, entitled SYSTEMS, METHODS, APPARATUSES, AND COMPUTER-READABLE MEDIA FOR IMAGE MANAGEMENT IN IMAGE-GUIDED MEDICAL PROCEDURES and U.S. patent application Ser. No. 13/753,274, filed Jan. 29, 2013, entitled MULTIPLE MEDICAL DEVICE GUIDANCE (the '274 application), and U.S. patent application Ser. No. 14/212,933, filed Mar. 14, 2014, entitled MEDICAL DEVICE GUIDANCE, each of which is hereby incorporated by reference in its entirety.

The system can aid the healthcare provider in guiding one or more medical devices through the tissue of the patient and/or placing the medical devices, and can be used for treatment of tumors, fibroids or cysts, with bipolar radiofrequency medical device ablation, multiple microwave medical devices, electroporation, and/or electrochemotherapy systems. It can also be used for nerve or muscle stimulation or sensing (electrodes in the spine, brain). The system can be used during open surgery, laparoscopic surgery, endoscopic procedures, biopsies, and/or interventional radiology procedures.

The system can be used in conjunction with live intraoperative ultrasound (U/S), pre-operative CT, or any cross-sectional medical imaging modality (e.g. MRI, OCT, etc.). In addition, the system can use a variety of techniques to determine the position and/or orientation of one or more medical devices. For example, the system can use the NDI Aurora magnetic system, NDI Polaris optical system, etc. In some embodiments, a position sensor can be embedded inside, or affixed to each medical device, at the tip, along the shaft, and/or on the handle. Sensors can be built into the medical devices or attached after manufacturing, as described in greater detail in U.S. application Ser. No. 14/212,184, filed Mar. 14, 2014, entitled SENSOR MOUNT, incorporated herein in its entirety.

Each medical device can be associated with one or more sensors, which can continually, or repeatedly, report position and/or orientation, or a single sensor can be used for all the medical devices. In embodiments where one sensor is used, the healthcare provider can attach the sensor to the particular medical device that she is intentionally repositioning, and then, once she has placed that medical device, she can remove the sensor and attach it to the next medical device she is repositioning. In some embodiments, the medical devices can be manipulated by the healthcare provider. In certain embodiments, the system can be used with a robotic manipulator, where the robot controls the medical devices.

In some embodiments, the handles of medical devices can have push-button switches, to allow the user to select a medical device, indicate a tissue target, etc. The handle can also have an indicator light to indicate to the users which medical device is selected. Finally, the handle can have an encoder to detect how much length of electrode has been exposed by the user, and report this information to the guidance system and therapeutic generator Image Guidance Systems FIG. 1 is a diagram illustrating an embodiment of a system for image management in image-guided medical procedures. In some embodiments, the position sensing unit 140 can track surgical instruments, also referred to herein as medical devices, within a tracking area and provide data to the image guidance unit 130. The medical devices can include invasive medical devices, such as, but not limited to, biopsy needles, ablation needles, surgical needles, nerve-block needles, or other needles, electrocautery device, catheters, stents, laparoscopes or laparoscopic cameras, ultrasound transducers, or other instruments that enter a part of the body, and non-invasive medical devices that do not enter the body, such as, but not limited to, ultrasound transducers, probes, or other external imaging devices, etc. The medical devices can also include medical imaging devices that provide or aid in the selection of medical images for display. In some embodiments, the medical imaging device can be any device that is used to select a particular medical image for display. The medical imaging devices can include invasive medical devices, such as laparoscopic cameras, and non-invasive medical devices, such as external ultrasound transducers.

Although only two surgical instruments 145 and 155 are shown in FIG. 1, it will be understood that additional surgical instruments can be tracked and associated data can be provided to the image guidance unit 130. The image guidance unit 130 can process or combine the data and show image guidance data on display 120. This image guidance data can be used by a healthcare provider to guide a procedure and improve care. There are numerous other possible embodiments of system 100. For example, many of the depicted components can be joined together to form a single component and can be implemented in a single computer or machine. Further, additional position sensing units can be used in conjunction with position sensing unit 140 to track all relevant surgical instruments 145 and 155, as discussed in more detail below. Additional imaging units 150 can be included, and combined imaging data from the multiple imaging units 150 can be processed by image guidance unit 130 and shown on display unit 120. Additionally, two or more surgical systems 149 can also be included.

Information about and from multiple surgical systems 149 and attached surgical instruments 145 (and additional surgical instruments not shown) can be processed by image guidance unit 130 and shown on display 120. These and other possible embodiments are discussed in more detail below. It will be understood that any combination of the display objects, image guidance cues, etc., described herein can be displayed concurrently, or simultaneously. Further, reference to displaying objects "concurrently" and/or "simultaneously" is to be interpreted broadly and may refer to displaying objects in such a way that to a human observer the objects are visible at the same time.

Imaging unit 150 can be coupled to image guidance unit 130. In some embodiments, imaging unit 150 can be coupled to a second display unit (not shown). The second display unit can display imaging data from imaging unit 150. The imaging data displayed on display unit 120 and displayed on second display unit can be the same or different. In some embodiments, the imaging unit 150 is an ultrasound machine 150, the movable imaging device 155 is an ultrasound transducer 155 or ultrasound probe 155, and the second display unit is a display associated with the ultrasound machine 150 that displays the ultrasound images from the ultrasound machine 150. In some embodiments, a movable imaging unit 155 can be connected to image guidance unit 130. The movable imaging unit 155 can be useful for allowing a user to indicate what portions of a first set of imaging data are to be displayed. For example, the movable imaging unit 155 can be an ultrasound transducer 155, a needle or other medical device, for example, and can be used by a user to indicate what portions of imaging data, such as a pre-operative CT scan, to show on a display unit 120 as image 125. Further, in some embodiments, there can be a third set of pre-operative imaging data that can be displayed with the first set of imaging data.

In some embodiments, system 100 comprises a display unit 120 and a position sensing unit 140 communicatively coupled to image guidance unit 130. In some embodiments, position sensing unit 140, display unit 120, and image guidance unit 130 are coupled to the stand 170. Image guidance unit 130 can be used to produce images 125 that are displayed on display unit 120. The images 125 produced on display unit 120 by the image guidance unit 130 can be determined based on ultrasound or other visual images from the first surgical instrument 145 and second surgical instrument 155. In the illustrated embodiment, the images 125 includes a 2D viewing area and a 3D viewing area. The 2D viewing area includes a 2D view of each of an ultrasound slice 121, a virtual medical device 122 corresponding to the first surgical instrument 145, a virtual imaging device 123 corresponding to the second surgical instrument 155, surface display regions 124a, 124b, intersection indicator 126, and trajectory and other image guidance cues 127. In the illustrated embodiment, the 3D viewing area includes perspective views of each of the image slice 121, the virtual medical device 122, a displayed affected region 129 including the surface display regions 124a, 124b, the virtual imaging device 123, intersection indicator 126, trajectory and other image guidance cues 127, and a patient orientation indicator 128. It will be understood that any combination of the aforementioned display objects can be displayed in the 2D view and/or 3D view as desired.

As a non-limiting example, if the first surgical instrument 145 is an ablation needle 145 and the second surgical instrument 155 is an ultrasound probe 155, then images 125 produced on display 120 can include the images, or video, from the ultrasound probe 155 (e.g., image slice 121) combined with other medical display objects and image guidance cues, such as projected medical device drive (e.g., trajectory indicators 127) or projected ablation volume (e.g., displayed affected region 129), determined based on the emplacement of ablation needle 145. If the first surgical instrument 145 is an ultrasound probe 145 and the second surgical instrument 155 is a laparoscopic camera 155, then images 125 produced on display 120 can include the video from the laparoscopic camera 155 combined with ultrasound data superimposed on the laparoscopic image. More surgical instruments can be added to the system. For example, the system can include an ultrasound probe, ablation needle, laparoscopic camera, stapler, cauterizer, scalpel and/or any other surgical instrument or medical device. The system can also process and/or display collected data, such as preoperative CT scans, X-Rays, MRIs, laser scanned 3D surfaces etc.

The term "emplacement" as used herein is a broad term and may refer to, without limitation, position and/or orientation or any other appropriate location information. The term "pose" as used herein is a broad term encompassing its plain and ordinary meaning and may refer to, without limitation, position and orientation or any other appropriate location information. In some embodiments, the imaging data obtained from one or both of surgical instruments 145 and 155 can include other modalities such as a CT scan, MRI, open-magnet MRI, optical coherence tomography ("OCT"), positron emission tomography ("PET") scans, fluoroscopy, ultrasound, or other preoperative, or intraoperative 2D or 3D anatomical imaging data. In some embodiments, surgical instruments 145 and 155 can also be scalpels, implantable hardware, or any other device used in surgery. Any appropriate surgical system 149 or imaging unit 150 can be attached to the corresponding medical instruments 145 and 155.

As noted above, images 125 produced can also be generated based on live, intraoperative, or real-time data obtained using the second surgical instrument 155, which is coupled to second imaging unit 150. The term "real time" as used herein is a broad term and has its ordinary and customary meaning, including without limitation instantaneously or nearly instantaneously. The use of the term real time can also mean that actions are performed or data is obtained with the intention to be used immediately, upon the next cycle of a system or control loop, or any other appropriate meaning. Additionally, as used herein, real-time data can be data that is obtained at a frequency that would allow a healthcare provider to meaningfully interact with the data during surgery. For example, in some embodiments, real-time data can be a medical image of a patient that is updated one time per second. In some embodiments, real-time data can be ultrasound data that is updated multiple times per second.

The surgical instruments 145, 155 can be communicatively coupled to the position sensing unit 140 (e.g., sensors embedded or coupled to the surgical instruments 145, 155 can be communicatively coupled with the position sensing unit 140). The position sensing unit 140 can be part of imaging unit 150 or it can be separate. The position sensing unit 140 can be used to determine the emplacement of first surgical instrument 145 and/or the second surgical instrument 155. In some embodiments, the position sensing unit 140 can include a magnetic tracker and/or one or more magnetic coils can be coupled to surgical instruments 145 and/or 155. In some embodiments, the position sensing unit 140 can include an optical tracker and/or one or more visually-detectable fiducials can be coupled to surgical instruments 145 and/or 155. In some embodiments, the position sensing unit 140 can be located below the patient. In such embodiments, the position sensing unit 140 can be located on or below the table 180. For example, in embodiments where the position sensing unit 140 is a magnetic tracker, it can be mounted below the surgical table 180. Such an arrangement can be useful when the tracking volume of the position sensing unit 140 is dependent on the location of the position sensing unit 140, as with many magnetic trackers. In some embodiments, magnetic tracking coils can be mounted in or on the medical devices 145 and 155.

In some embodiments, the position sensing unit 140 can be an electromagnetic measurement system (e.g., NDI Aurora system) using sensor coils for tracking units attached to the first and/or second surgical devices 145 and 155. In some embodiments, the second position sensing unit 140 can be an optical 3D tracking system using fiducials. Such optical 3D tracking systems can include the NDI Polaris Spectra, Vicra, Certus, PhaseSpace IMPULSE, Vicon MX, InterSense IS-900, NaturalPoint OptiTrack, Polhemus FastTrak, IsoTrak, or Claron MicronTracker2. In some embodiments, the position sensing unit 140 can each be an inertial 3D tracking system comprising a compass, accelerometer, tilt sensor, and/or gyro, such as the InterSense InertiaCube or the Nintendo Wii controller. In some embodiments, the position sensing unit 140 can be attached to or affixed on the corresponding surgical device 145 and 155.

In some embodiments, the position sensing units 140, can include sensing devices such as the HiBall tracking system, a GPS device, or signal emitting device that would allow for tracking of the position and/or orientation (e.g., emplacement) of the tracking unit (also referred to as an emplacement sensor). In some embodiments, a position sensing unit 140 can be affixed to either or both of the surgical devices 145 and 155. The surgical devices 145 or 155 can be tracked by the position sensing unit 140. A room coordinate system reference, such as the display 120 can also be tracked by the position sensing unit 140 in order to determine the emplacements of the surgical devices 145 and 155 with respect to the room coordinate system. Devices 145 and 155 can also include or have coupled thereto one or more accelerometers, which can be used to estimate movement, position, and location of the devices.

In some embodiments, the position sensing unit 140 can be an Ascension Flock of Birds, Nest of Birds, driveBAY, medSAFE, trakSTAR, miniBIRD, MotionSTAR, pciBIRD, or Calypso 2D Localization System and tracking units attached to the first and/or second medical devices 145 and 155 can be magnetic tracking coils.

The term "tracking unit" (also referred to as an emplacement sensor), as used herein, is a broad term encompassing its plain and ordinary meaning and includes without limitation all types of magnetic coils or other magnetic field sensing devices for use with magnetic trackers, fiducials or other optically detectable markers for use with optical trackers, such as those discussed above and below. In some embodiments, the tracking units can be implemented using optical position sensing devices, such as the HiBall tracking system and the position sensing unit 140 can form part of the HiBall tracking system. Tracking units can also include a GPS device or signal emitting device that allows for tracking of the position and/or orientation of the tracking unit. In some embodiments, a signal emitting device might include a radio-frequency identifier (RFID). In such embodiments, the position sensing unit 140 can use the GPS coordinates of the tracking units or can, for example, triangulate the radio frequency signal being emitted by the RFID associated with tracking units. The tracking systems can also include one or more 3D mice.

Images 125 can be produced based on intraoperative or real-time data obtained using first surgical instrument 145, which is coupled to first surgical system 149. In the illustrated embodiment of FIG. 1, the first surgical system 149 is shown as coupled to image guidance unit 130. The coupling between the first surgical system 149 and image guidance unit 130 may not be present in all embodiments. In some embodiments, the coupling between first surgical system 149 and image guidance unit 130 can be included where information about first surgical instrument 145 available to first surgical system 149 is useful for the processing performed by image guidance unit 130. For example, in some embodiments, the first surgical instrument 145 is an ablation needle 145 and first surgical system 149 is an ablation system 149. In some embodiments, it can be useful to send a signal about the relative strength of planned ablation from ablation system 149 to image guidance unit 130 in order that image guidance unit 130 can show a predicted ablation volume. In other embodiments, the first surgical system 149 is not coupled to image guidance unit 130. Example embodiments including images and graphics that can be displayed are included below.

In some embodiments, the display unit 120 displays 3D images to a user, such as a healthcare provider. Stereoscopic 3D displays separate the imagery shown to each of the user's eyes. This can be accomplished by a stereoscopic display, a lenticular auto-stereoscopic display, or any other appropriate type of display. The display 120 can be an alternating row or alternating column display. Example alternating row displays include the Miracube G240S, as well as Zalman Trimon Monitors. Alternating column displays include devices manufactured by Sharp, as well as many "auto-stereoscopic" displays (e.g., Philips). In some embodiments, Sony Panasonic 3D passive displays and LG, Samsung, and/or Vizio 3D TVs can be used as well. Display 120 can also be a cathode ray tube. Cathode Ray Tube (CRT) based devices, can use temporal sequencing, showing imagery for the left and right eye in temporal sequential alternation. This method can also be used projection-based devices, as well as by liquid crystal display (LCD) devices, light emitting diode (LED) devices, and/or organic LED (OLED) devices.

In certain embodiments, the display unit 120 can be a head mounted display worn by the user in order to receive 3D images from the image guidance unit 130. In such embodiments, a separate display, such as the pictured display unit 120, can be omitted. The 3D graphics can be produced using underlying data models, stored in the image guidance unit 130 and projected onto one or more 2D planes in order to create left and right eye images for a head mount, lenticular, or other 3D display. The underlying 3D model can be updated based on the relative emplacements of the various devices 145 and 155, as determined by the position sensing unit(s) 140, and/or based on new data associated with the devices 145 and 155. For example, if the second medical device 155 is an ultrasound probe, then the underlying data model can be updated to reflect the most recent ultrasound image. If the first medical device 145 is an ablation needle, then the underlying model can be updated to reflect any changes related to the needle, such as power or duration information. Any appropriate 3D graphics processing can be used for rendering including processing based on OpenGL, Direct3D, Java 3D, etc. Whole, partial, or modified 3D graphics packages can also be used, such packages including 3DS Max, SolidWorks, Maya, Form Z, Cybermotion 3D, VTK, Slicer, or any others. In some embodiments, various parts of the needed rendering can occur on traditional or specialized graphics hardware. The rendering can also occur on the general CPU, on programmable hardware, on a separate processor, be distributed over multiple processors, over multiple dedicated graphics cards, or using any other appropriate combination of hardware or technique.

One or more components, units, devices, or elements of various embodiments can be packaged and/or distributed as part of a kit. For example, in one embodiment, an ablation needle, one or more tracking units, 3D viewing glasses, and/or a portion of an ultrasound wand can form a kit. Other embodiments can have different elements or combinations of elements grouped and/or packaged together. Kits can be sold or distributed separately from or with the other portions of the system.

One will readily recognize that there are numerous other examples of image guidance systems which can use, incorporate, support, or provide for the techniques, methods, processes, and systems described herein.

Depicting Surgical Instruments

It can often be difficult to discern the content of a 3D scene from a 2D depiction of it, or even from a 3D depiction of it. Therefore, various embodiments herein provide image guidance that can help the healthcare provider better understand the scene, relative emplacements or poses of object in the scene and thereby provide improved image guidance.

Figure 2:
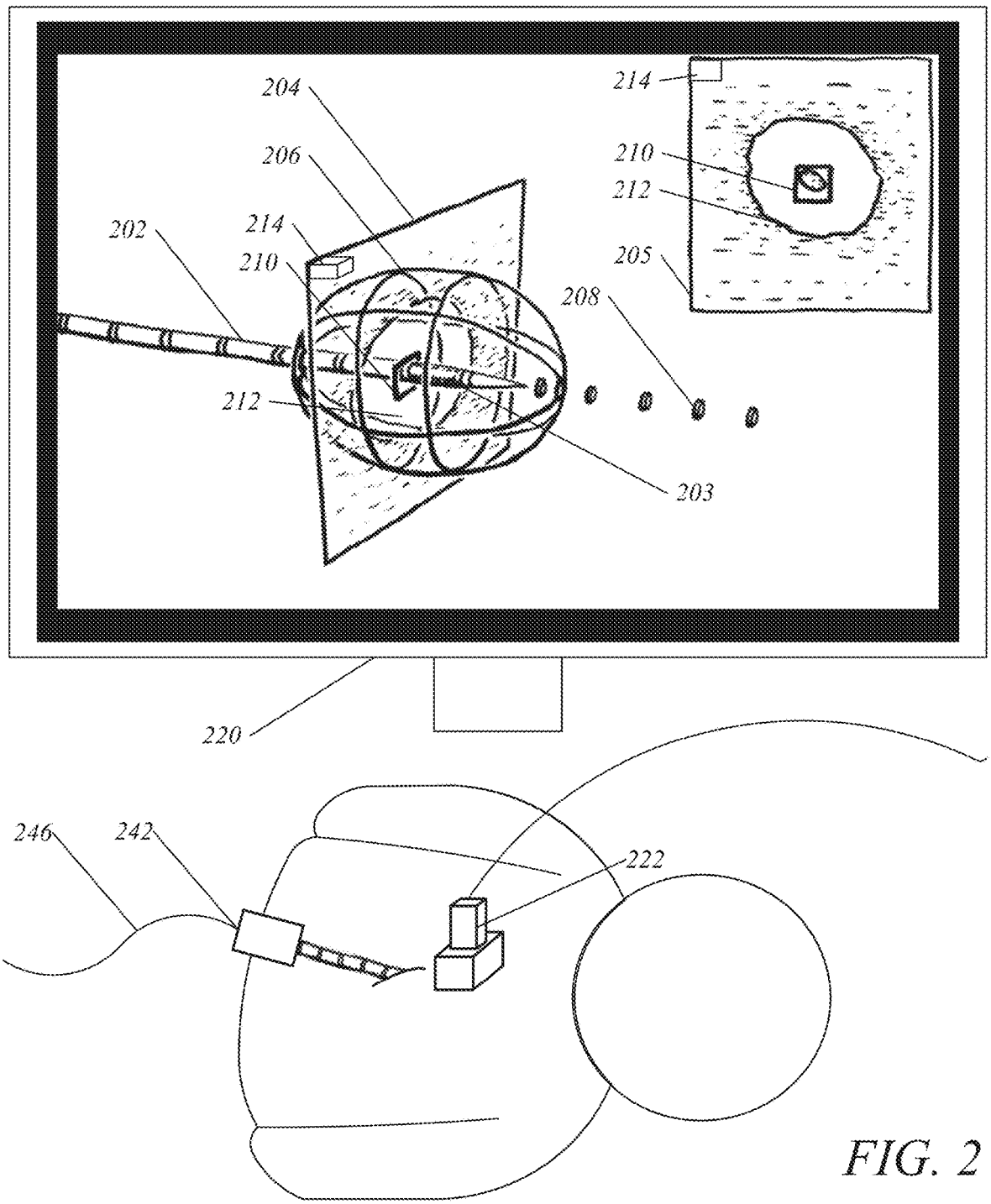
FIG. 2 is a diagram of an embodiment of a rendering of image guidance cues and medical display objects on a display.

FIG. 2 illustrates a perspective view of a virtual rendering 202 of a surgical instrument 242 being displayed on a screen 220 with a perspective view of a medical image 204. In some embodiments, the screen 220 can correspond to the screen of a display unit 120, which can be implemented using a TV, computer screen, head-mounted display, projector, etc. In the illustrated embodiment, the rendered surgical instrument 202 displayed on the screen 220 corresponds to the ablation needle 242. A wire 246 connecting the ablation needle 242 to an ablation system is also depicted in FIG. 2.

Although only one virtual surgical instrument 202 is displayed, it will be understood that multiple medical devices can be tracked and displayed concurrently, or simultaneously, on screen 220, as described in greater detail in the '274 application, previously incorporated by reference. For example, a virtual rendering of the medical imaging device 222 can be displayed.

The virtual surgical instrument 202 can be displayed in a virtual 3D space with the screen 220 acting as a window into the virtual 3D space. Thus, as the surgical instrument 242 is moved to the right with respect to a point-of-view location (e.g., the location of the point-of-view for viewing the 3D space), the virtual surgical instrument 202 also moves to the right. Similarly, if the surgical instrument 242 is rotated 90 degrees so that the tip of the surgical instrument is pointing away from the point-of-view location (e.g., at the screen 220), the virtual surgical instrument 201 will likewise show the change in orientation, and show the tip of the virtual surgical instrument 202 in the background and the other end of the virtual surgical instrument 202 in the foreground. In some embodiments, as described in greater detail in U.S. application Ser. No. 14/212,933, incorporated herein by reference in its entirety, the point-of-view location can be a fixed location, such as a predetermined distance/angle from the screen 220 or stand 170 and or a location configured by the user; or the point-of-view location can by dynamic. For example, the system can track a user in real-time and determine the point-of-view location based at least in part on the tracked location of the user.

Some models of medical devices have markings such as bands around the shaft (to indicate distance along the shaft), and a colored region 203 near the tip to indicate from where the radio frequency or microwave energy is emitted in the case of an ablation probe. Healthcare providers performing medical device procedures are often familiar with these markings and can use them to help understand the spatial relationship between the medical device and anatomy. In some embodiments, the make and model of the medical device 242 is known to the image guidance system and the virtual medical device 202 displayed in display 220 can resemble medical device 242. The features of medical devices that can be rendered in the scene include the overall shape (diameter, cross sectional shape, curvature, etc.), color, distance markers, visuals or echogenic fiduciary markers, the state of deployable elements such as tines, paddles, anchors, resection loops, stiffening or steerable sleeves, temperature, radiation, light or magnetic field sensors, lens, waveguides, fluid transfer channels, and the like.

The type of medical device being used can be input into the image guidance system 100, can be a system default, can be detected by a camera or other device, can be received as data from an attached medical device, such as surgical system 149 in FIG. 1, or the information can be received in any other appropriate manner. Displaying on display 220, a virtual surgical instrument that resembled the surgical instrument 242 can help healthcare providers associate the image guidance data with the real world and can provide more familiar guidance information to a healthcare provider, thereby further aiding the healthcare provider in the guidance task. For example, the healthcare provider can see the familiar markings on the medical device being displayed on the display 220 and therefore be familiar with the distance and relative placement of the displayed medical device with respect to other data, such as a tumor 212 seen in a rendered ultrasound image 204, 205. This knowledge of relative placement of items being displayed can help the healthcare provider move the medical device into place.

Consider an embodiment in which the virtual surgical instrument 202 in the display 220 is an ablation needle depicting the portion of the needle that will perform the ablation, for example, the portion that emits the radio or microwave energy. If the display 220 also includes ultrasound data, then the doctor can be able to find the tumor 212 she wishes to ablate by moving the ultrasound probe around until she spots the tumor 212. In various embodiments, she will be able to see the displayed ultrasound data and its location relative to the displayed medical device with the markings. She can then drive the medical device until she sees, on display 220, that the emitter-portion of the medical device encompasses the tumor in the ultrasound, also seen on display 220. When she activates the ablation, she can then be much more certain that she has ablated the correct portion of the tissue. Various embodiments of this are discussed below.

As another example, consider the physical markings that can be on the instruments themselves. These markings can help orient a healthcare provider during use of the instrument. In some embodiments, the image guidance unit can represent these markings in the images displayed in the display. For example, certain ultrasound transducers are built with an orientation mark (e.g., a small bump) on one side of the transducing array. That mark can also be shown in the ultrasound image on the scanner's display, to help the healthcare provider understand where the scanned anatomical structures shown on screen are located under the transducer, inside the patient. In some embodiments, the image guidance system can display a symbolic 3D representation of the orientation mark both next to the motion-tracked ultrasound slice (e.g., moving with the displayed ultrasound slice) and next to the 2D view of the ultrasound slice also displayed by the system. An example of this is displayed in FIG. 2, where a small rectilinear volume 214 corresponding to a feature on an ultrasound probe is shown both in proximity to the ultrasound slice displayed in the 3D view and the ultrasound slice displayed in a 2D view.

It will be understood that an image slice can correspond to image data received from an imaging device, such as an ultrasound transponder. In some embodiments, the image data can correspond to a cross-section of tissue having a certain thickness. In some instances, the imaging device can compact the image data, and/or treat the image data as 2D data, such that there is no perceived thickness. In certain embodiments, when the image slice is displayed in a 3D view, the system can treat the image slice as a 2D or quasi 2D object. In such embodiments, the system can cause the image slice to have little to no perceptible thickness. Accordingly, in certain embodiments, when the image slice is oriented orthogonally or perpendicularly with respect to the point-of-view location, the system can cause the display to display nothing or a line having a relatively small thickness, such as a few pixels, etc. In some cases, the number of pixels used to display the relatively small thickness of the image slice can correspond to the size of the display. For example, more pixels can be used for a larger display and fewer pixels can be used for a smaller display, etc.

Other embodiments can track and display other types of instruments and their features. For example, a healthcare provider may want to track one or more of a scalpel, a biopsy, a cauterizer (including an electrocauterizer and Bovies), forceps, cutting loops on hysteroscopes, harmonic sheers, lasers (including $CO_2$ lasers), etc. For example, in various embodiments, the following devices can be tracked and various aspects of their design displayed on display 220: Olympus™ OES Pro Hystero-Resectoscope, SonoSurg Ultrasonic Surgical System Olympus™ GF-UC 160 Endoscope Wallus™ Embryo Transfer Catheter AngioDynamics® NanoKnife™, VenaCure™ laser, StarBurst, Uniblade, Habib® Resector Bovie™ Electrodes, Covidien Evident™, Cool-Tip™ Ablation Antennas, Opti4™ Electrodes Microsulis MEA (microwave endometrial ablation), Acculis Halt™ Medical System Optimed BigLumen Aspiration Catheter Optimed Optipure Stent Central venous catheterization introducer medical device (such as those made by Bard and Arrow).

Once tracked, a healthcare provider is able to see image guidance data on display 220 that will allow her to know the relative pose, location, or emplacement of the tracked instrument(s) with respect to one another or with respect to imaging data and will be able to see, on display 220, the features of the instrument rendered in the scene.

Depicting Medical Device Placement, Trajectory, and Other Image Guidance Cues

In certain procedures, the system can provide image prediction information related to the surgical instruments as image guidance cues. In the context of scalpel movement, this can be the location that the scalpel will hit if a healthcare provider continues to move the scalpel in a particular direction. In the context of ablation or biopsies, this can be the projected medical device placement if it is driven along its central axis, which is also referred to herein as a longitudinal axis.

FIG. 2 further illustrates an embodiment of a projected needle drive 208 (also referred to as a trajectory indicator) as an image guidance cue. If a healthcare provider is driving an ablation needle 242 into tissue (not pictured), then she can know where the medical device will be driven. In some embodiments, the projected drive 208 of a medical device can be depicted on the display 220 and can show the healthcare provider the projected path 208 that the medical device 242 will take if it is driven along its central axis. Although the trajectory of only one medical device is displayed, it will be understood that the trajectory of multiple medical devices can be determined and displayed simultaneously on screen 220, as described in greater detail in the '274 application.

In some embodiments, to implement the trajectory indicators 208, the image guidance system can draw a number of rings about the axis of the medical device shaft, extrapolated beyond its tip, as depicted in FIG. 4. A healthcare provider can view and manipulate the emplacement of the medical device 242 and its expected drive projection (via its displayed projected trajectory) before it enters the patient's tissue. In some embodiments, this is accomplished by the doctor positioning the virtual rings in the drive projection such that they are co-incident (or pass through) the ultrasound representation of a target, such as a tumor that the doctor has spotted in the ultrasound. This can allow the healthcare provider to verify that the medical device 242 is properly aimed at the target and can drive the medical device 242 forward into the tissue such that it reaches its desired target or destination. For example, if the doctor identifies a tumor 212 in the ultrasound image, she can align the ablation needle 242 such that the drive projection rings on display 220 intersect or otherwise indicate that the medical device, if driven straight, will reach the tumor 212.

The rings can, in some embodiments, be spaced at regular (e.g., 0.5, 1, or 2 cm) intervals to provide the healthcare provider with visual or guidance cues regarding the distance from the medical device tip to the targeted anatomy. In some embodiments, the spacing of the rings can indicate other aspects of the data, such as the drive speed of the medical device, the density of the tissue, the distance to a landmark, such as the ultrasound data, or any other appropriate guidance data or property. In some embodiments, the rings or other trajectory indicators can extend beyond the medical device tip, by a distance equal to the length of the medical device-shaft. This way, the user knows if the medical device is long enough to reach the target—even before the tip enters the patient. That is, in some embodiments, if the rings do not reach the target with the tip still outside the body, then the tip will not reach the target even when the entire length shaft is inserted into the body.

Other display markers can be used to show trajectory, such as a dashed, dotted, or solid line, transparent medical device shaft, point cloud, wire frame, etc. In some embodiments, three-dimensional rings can be used and provide depth cues and obscure little of the ultrasound image. Virtual rings or other virtual markers can be displayed semi-transparently, so that they obscure less of the ultrasound image than an opaque marker would.

Other prediction information can also be displayed as image guidance cues. For example, if a scalpel is being tracked by the image guidance system, then a cutting plane corresponding to the scalpel can be displayed (not pictured). Such a cutting plan can be coplanar with the blade of the scalpel and can project from the blade of the scalpel. For example, the projected cutting plane can show where the scalpel would cut if the doctor were to advance the scalpel. Similar prediction information can be estimable or determinable for cauterizers, lasers, and numerous other surgical instruments.

Furthermore, the data from two or more devices can be combined and displayed based on their relative emplacements or poses. For example, the system 100 can determine the emplacement of an image plane based on the emplacement information of the ultrasound probe 222. Further, the rendered ultrasound image 204 can be displayed on the image plane with respect to the virtual medical device 202 on the display 220 in a manner that estimates the relative emplacements or poses of an ultrasound probe 222 and the medical device 242. As illustrated in FIG. 2, the image guidance cues associated with the virtual medical device 202, including the affected region indicator 206 and trajectory indicators 208, are shown spatially located with the rendered ultrasound image 204 on display 220.

In addition, the display 220 can include another image guidance cue in the form of an intersection indicator 210 that indicates where the virtual ablation medical device 202 (and/or its trajectory) intersects the ultrasound image 204. In some embodiments, the intersection indicator 210 can be displayed before the medical device is inserted, thereby allowing the healthcare provider to see where the medical device will intersect the image, or imaged area.

In the illustrated embodiment, a tumor 212 appears in the ultrasound image, or rendered ultrasound image 204, and the virtual ablation needle 202 is shown driven through the tumor 212. As will be described in greater detail below, the displayed affected region (or affected region indicator) 206 can indicate what region or volume would be affected when the medical device 242 is operated. In the illustrated embodiment, the displayed affected region 206 can estimate where ablation would occur if the tissue were ablated at that time. As can be seen, in the illustrated embodiment, the displayed affected region 206 appears to cover the tumor displayed in the ultrasound image.

Various embodiments can include any combinations of the graphics described above and/or other graphics or image guidance cues. For example, in some embodiments, data related to a single surgical instrument (such as an ablation needle, ultrasound probe, etc.) can be presented in more than one manner on a single display. Consider an embodiment in which device 242 is an ablation needle and device 222 is an ultrasound transducer. As mentioned previously, as the medical devices are displayed in a virtual 3D space, with the screen 220 acting as a window into the virtual 3D space, if a healthcare provider orients ultrasound transducer 222 such that it is perpendicular to the point-of-view or point-of-view location (e.g., perpendicular to the screen), the perspective view of the ultrasound image 204 would show only the edge and the contents of the ultrasound image 204 would not be visible. In some embodiments, the image guidance system can track the healthcare provider's head using an emplacement sensor and/or a position sensing unit. In some embodiments, such as, when the head of a user is tracked, the healthcare provider can then move her head to the side, so that she sees the ultrasound image from a different point of view location.

In some embodiments, the image guidance system can constantly display an additional 2D view 205 of the ultrasound image, simultaneous to the 3D depiction 204, so that the ultrasound image is always visible, regardless of the emplacement in which the healthcare provider holds the transducer 222. The 2D view 205 of the ultrasound data can be similar to what a healthcare provider is accustomed to seeing with traditional ultrasound displays. This can be useful to provide the healthcare provider with imaging to which she is accustomed and allows a healthcare provider to see the ultrasound data regardless of the then-current emplacement of the ultrasound probe with respect to the user.

In some embodiments, the 2D view 205 of an ultrasound image is depicted in the upper right corner of the monitor (though it can be placed in any location). In some embodiments, the guidance system can automatically (and continually) choose a corner in which to render the 2D view 205 of the ultrasound image, based on the 3D position of the surgical instruments in the rendered scene. For example, in FIG. 2, ablation needle 242 can be held in the healthcare provider's left hand and the medical device shaft is to the left of the 3D view of the ultrasound image slice, so that the 2D view 202 of the ultrasound image in the upper right corner of display 220 does not cover any of the 3D features of the medical device (or vice-versa). If the medical device were held in the healthcare provider's right hand, the virtual medical device shaft would appear on the right side. To prevent the 2D view 205 in the corner of display 220 from covering the medical device shaft, the system can automatically move it to a corner that would not otherwise be occupied by graphics or data.

In some embodiments, the system attempts to avoid having the 2D view 205 of the ultrasound image quickly moving among corners of the display in order to avoid overlapping with graphics and data in the display. For example, a function f can be used to determine which corner is most suitable for the 2D ultrasound image to be drawn in. The inputs to f can include the locations, in the screen coordinate system, of the displayed medical device tip, the corners of the 3D view of the ultrasound image, etc. In some embodiments, f's output for any given point in time is independent of f's output in the previous frames, which can cause the ultrasound image to move among corners of the display rapidly. In some embodiments, the image guidance system will filter f's output over time. For example, the output of a filter g, for any given frame, could be the corner, which has been output by f the most number of times over the last n frames, possibly weighting the most recent values for f most heavily. The output of the filter g can be used to determine in which corner of display 220 to display the 2D ultrasound image and the temporal filtering provided by g can allow the 2D view 205 of the ultrasound image display to move more smoothly among the corners of the display 220.

In some embodiments, other appropriate virtual information and/or image guidance cues can be overlaid on the 2D view 205 of the ultrasound image as well as the 3D view 204. Examples include: orientation indicator 214, an indication of the distance between the medical device's tip and the point in the plane of the ultrasound image that is closest to the medical device tip; the cross section or outline of the ablation volume that intersects with the ultrasound slice; and/or the intersection point, box, outline, etc. between the medical device's axis and the ultrasound image plane.

Furthermore, it will be understood that other image guidance cues can be generated and displayed on the display as described in greater detail in the '274 application, previously incorporated herein by reference. For example, the system 100 can generate and/or display graphical indicators that help indicate the spatial relationship between a medical device and an ultrasound image plane (e.g., graphical image plane indicators) or other plane (e.g., graphical plane indicators), indicators to indicate the relative positions of the medical device(s) and ultrasound image, features of interest, annotations, foundational plane indicators, foundational plane intersection indicators, other graphical indicators, approximate medical device location indicators, etc. As described in greater detail above and in the '274 application, the various image guidance cues can be generated based at least in part on the emplacement information of the medical devices used with the system 100.

Depicting Affected Region and Other Information

Embodiments of the system can include image guidance cues as part of the image guidance data to depict information related to the region or regions that will be affected by the use of surgical instruments. For example, in some embodiments, an image guidance cue displayed by the image guidance system can include affected region information. The illustrated embodiment of FIG. 2 shows a virtual ablation needle 202, which has a darkened portion 203 that indicates where the radio frequency or microwave energy for ablation will be emitted, and a displayed affected region 206 showing the volume that will be, or is being, ablated.

In some embodiments, the system can use the operating parameters of the medical device 242 and/or measured parameters to determine the affected region (and display the displayed affected region 206). For example, in some cases, the affected region's approximate size (e.g., girth and length) can be either specified by the healthcare provider, or automatically computed by the guidance system based on or more operating parameters, such as, but not limited to, the medical device make and model, power and duration settings of the medical device (e.g., microwave or radio frequency generator for ablation needles, etc.), and the like. Similarly, the system can use measured parameters to determine the affected region, such as, but not limited to, measured or estimated temperature, impedance of surrounding tissue. In some embodiments, the measured parameters can be received in real-time as real-time data. In either case, the system can use one or more a formulas, a look-up-tables, fixed or default values, or any other appropriate available information, etc. to determine the affected region.

In addition, the system can determine affected regions prior to operating the medical device and/or during operation of the medical device. For example, prior to operating the medical device, the system can determine one or more predicted affected regions and/or during operation of the medical device, the system can determine one or more dynamic affected regions. In some embodiments, the predicted affected regions can be static during operation of the medical device and the dynamic affected regions can change over time. In certain embodiments, the system may rely more on operating parameters of the medical device to determine the predicted affected regions and measured parameters to determine the dynamic affected regions. However, it will be understood that operating parameters and/or measured parameters can be used to determine the predicted affected regions and/or the dynamic affected regions In some circumstances, the operating parameters, measured parameters, formulas, a look-up-tables, fixed or default values, or other information used to determine the affected regions may include some amount of error or variance. The variance may be due to uncertainty regarding the tissue that will be presented for ablation, a manufacturers indication that impedance, temperature, power, etc., can vary between tissue and/or medical devices, etc.

As such, it can be difficult to determine the affected region with certainty. Thus, the operating parameters or other data can include one or more variance parameters indicating the amount of variance that a healthcare provider can expect when using a particular medical device. The variance parameter may account for all possible outcomes or a significant portion of possible outcomes (non-limiting examples: 95% or 99%). For example, the variance parameter can indicate that a medical device operates within a certain range, or that a healthcare provider can expect a certain volume to be affected with a particular standard deviation and/or +/−some percent. For example, the variance parameter may indicate that, when operating for a particular amount of time, an ablation needle will ablate a certain range of tissue, or that a certain amount of tissue will be ablated with a particular standard deviation and/or +/−some percent.

Accordingly, in such scenarios, the system can determine multiple affected regions based at least in part on the variance parameter. For example, the system can determine two affected regions using the extrema of the variance parameter. In some cases, such as when the variance parameter includes a lower threshold and a higher threshold, the system can determine two affected regions using the lower threshold and the higher threshold, respectively. The affected regions can be predicted affected regions and/or dynamic affected regions depending on when and how the system determines them. In some cases, a third affected regions can be determined. The third affected region can be determined using a third point in the range, such as the midpoint, average, or other point.

The system can also determine the emplacement of the affected region. In some cases, the emplacement of the affected region can be based at least in part on the emplacement of some or all of the corresponding medical device (or virtual medical device), such as medical device 242 in FIG. 2. For example, the system can receive emplacement data from one or more emplacement sensors associated with the medical device 242 (non-limiting examples: coupled to or integrated with the medical device 242, within an optical path of the medical device, etc.). The system can use the emplacement data to determine the emplacement of the tracked medical device and/or the emplacement of the virtual medical device 202 corresponding to the medical device 242. In some instances, the system can determine the emplacement of the medical device 242 and/or virtual medical device 202 with respect to a point-of-view location.

As yet another example, if the medical device is an ablation needle and the affected region is an ablation volume, the emplacement of the ablation volume can be based at least in part on the emplacement of the ablation needle (or its rendered version) or at least a portion of it, such as the location on the ablation needle where the ablation energy will be emitted. Specifically, in some embodiments, the affected region can be centered at a location on the medical device, such as the location on the medical device that affects the surrounding tissue (non-limiting examples: microwave emitter, laser source output, etc.). Similarly, if multiple medical devices are used, the posed can be based at least in part on the emplacement of the medical devices.

The system can display the affected region in a variety of ways. Furthermore, although the illustrated embodiment of FIG. 2 includes only one displayed affected region 206, it will be understood that one or more affected regions can be displayed corresponding to each medical device 242 that is displayed on the screen 220 and/or multiple affected regions can be displayed corresponding to a single medical device 242. In some embodiments, the system can display a perspective view of the affected region and/or non-perspective view, such as by displaying the affected region on or with the ultrasound image displayed in the 2D view. Some or all of the affected regions can be displayed as desired. In some embodiments, the portion of the affected region that is displayed can be referred to as the displayed affected region and/or the surface display region.

For some medical devices, the expected volume of ablated tissue is neither spherical nor centered at the tip of the medical device. Accordingly, in such embodiments, the affected regions can match expected volumes. For example, a Covidien surgical microwave medical device has an ellipsoidal ablation volume; a Covidien Evident transcutaneous microwave medical device has a teardrop-like ablation volume; RFA Medical's bipolar ablation system uses two medical devices simultaneously, where each medical device has paddles that deploy after the medical device is inserted inside the tissue (which one can equate to a canoe's oar). In some embodiments, the affected region for such a medical device corresponds to a volume that lies directly between the paddles of the two medical devices.

Although the illustrated embodiment of FIG. 2 refers to the affected region as an ablation volume, it will be understood that the affected region can correspond to a variety of medical procedures. For example, if a cauterizer is tracked as part of an image guidance system, then the affected region can correspond to a cauterization volume. If a laser is tracked as part of the image guidance system, then the affected region can correspond to the projected laser path. Similarly, the affected region can correspond to a biopsy volume, an electroporated volume, cryoablation volume, laser ablation volume, high-frequency focused ultrasound ablation (HIFU) volume, external beam radiation therapy volume, and drilling volume (where the display volume corresponds to the region of bone and other tissue that the manually operated, or computer-controlled drill would remove), depending on the type of medical instrument being used.

Example Displayed Affected Regions

As non-limiting examples and with reference to FIGS. 3A-3J, 4A-4C, and 5A-5C, the system can display the affected regions as a transparent volume, a wireframe volume (as depicted in FIG. 2), a volume with varying opacity, a point cloud of various densities, a surface, an outline, or any portion thereof. As mentioned above, the affected regions can correspond to predicted affected regions and/or dynamic affected regions, as desired.

When displaying a portion of a volume, the system can display the portions of the volume that are located in front of the image slice with respect to the point-of-view location (or display them differently than portions that are behind the image slice), alternating bands or tiles of the affected region, portions of the affected region that are co-located with or intersect the medical device and/or the image slice. In addition, when multiple affected regions are determined, the system can display them in any combination as described above. Further, in some embodiments, such as when the system determines a second affected region that includes a first affected region, the displayed affected region can include the portions of the second affected region that are unique second affected region with respect to the first affected region only, or in combination with other portions. In certain embodiments, such as when the system determines that portions of a second affected region and a first affected region overlap, the system can display the overlapping portions only, or in combination with other portions.

Furthermore, the system can display the affected regions and other displayed features differently. For example, in some embodiments, the system can vary the characteristics of the affected regions (non-limiting examples: portions closer to the outline or edge of the affected regions can be more/less opaque, bright or focused, distal portions of the affected regions can be more/less opaque, bright or focused). Similarly, the system can vary the characteristics of the other displayed features. In some embodiments, the system can use different display settings for different portions of an image slice. For example, the system can display portions of the image slice within a first affected region using a first setting, portions of the image slice within a second affected region using a second setting, and portions of the image slice outside the first and second affected regions using a third setting. The different settings can correspond to different opacity levels, brightness levels, contrast levels, and/or focus levels, etc. In some embodiments, portions of the image slice outside the first and second affected regions can be darkened, blurred, or otherwise adjusted to provide the healthcare provider with additional insight regarding the portions of the image slice that are within the affected region(s).

Figure 3A:
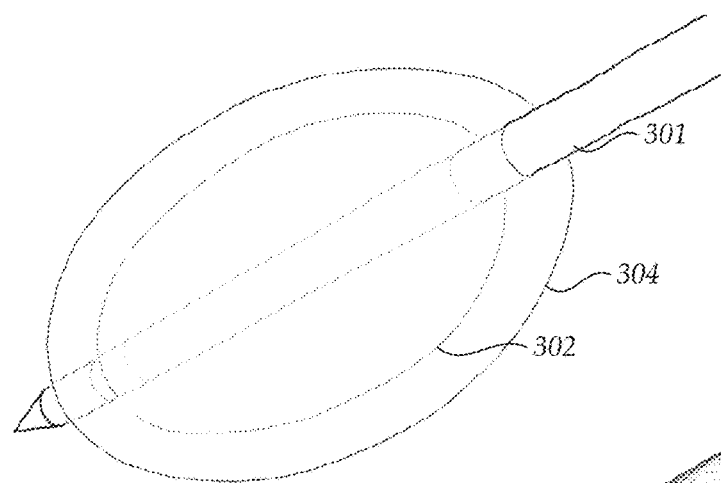
FIGS. 3A, 3B, 3C, 3D, 3E, 3F, 3G, 3H, 3I, and 3J are diagrams illustrating embodiments of displayed affected regions.
Figure 3B:
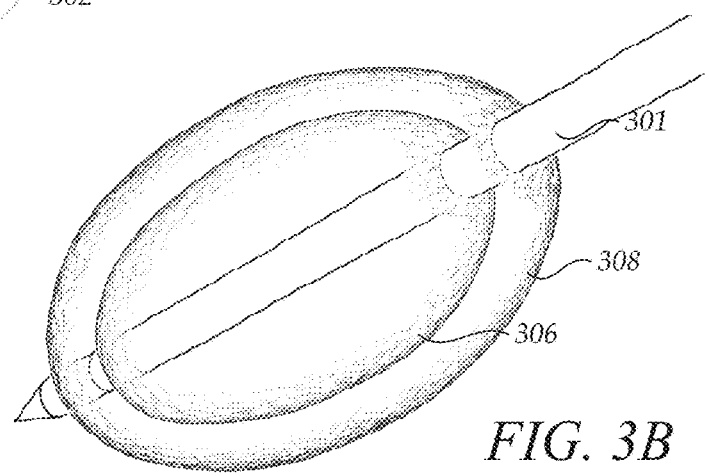

FIGS. 3A-3J are diagrams illustrating various non-limiting embodiments for displaying a perspective view of at least a portion of the affected regions as a volume. FIG. 3A illustrates an embodiment in which two affected regions are displayed as two transparent volumes 302, 304 and/or outlines along with a virtual medical device 301. FIG. 3B illustrates an embodiment in which two affected regions are displayed as two volumes 306, 308 with varying opacity (or as semi-transparent). In the illustrated embodiment, the volumes 306, 308, are more opaque near the edges, however, it will be understood that the opacity can be varied throughout the volumes 306, 308 as desired.

Figure 3C:
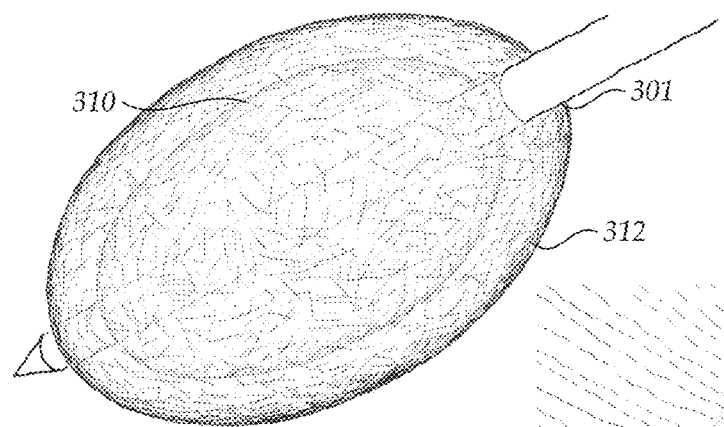
Figure 3D:
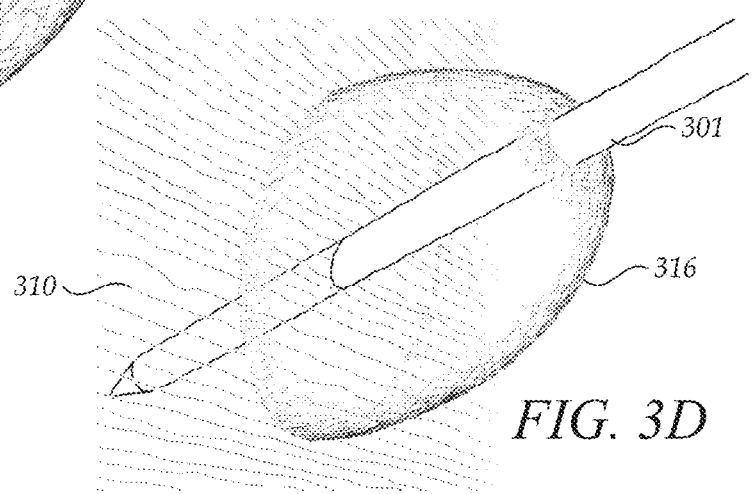

FIG. 3C illustrates an embodiment in which two affected regions are displayed as two volumes 310, 312 with a surface texture. FIG. 3D illustrates an embodiment in which a portion of the affected region that is located between the image slice 314 and the point-of-view location (or in front of the image slice 314) is displayed as a volume 316. It will be understood that the portion of the affected region that is located between the image slice 314 and the point-of-view location can be displayed differently from portions of the affected region that is located distally from the point-of-view location with respect to the image slice 314. For example, the different portions can be displayed with different colors, brightness, sharpness, etc. In some cases, the portions of the affected region located distally from the point-of-view location with respect to the image slice 314 can be displayed with lighter or more faded colors, etc.

Figure 3E:
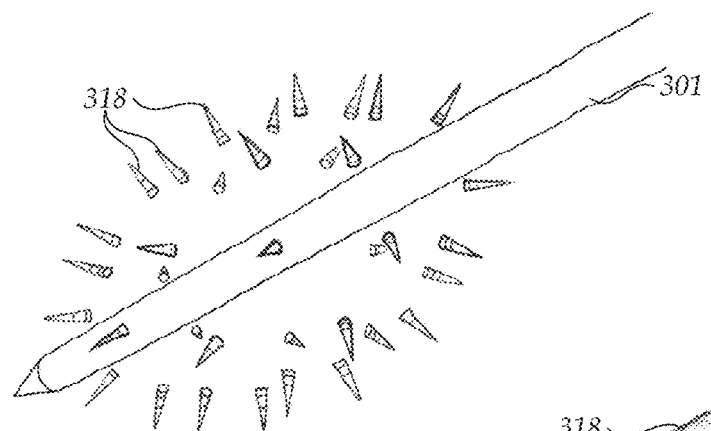
Figure 3F:
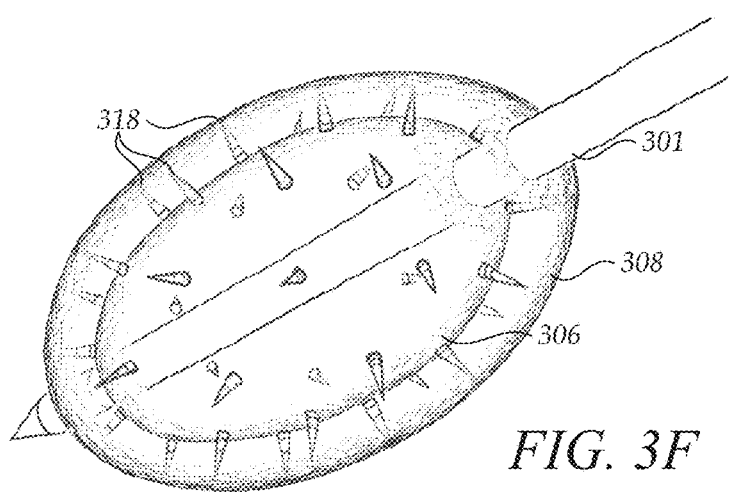

FIG. 3E illustrates an embodiment in which portions of a second affected region are displayed. The portions displayed correspond to the portions of the second affected region that are unique to the second affected region with respect to the first affected region. In the illustrated embodiment, the portions are displayed as spikes 318. However, it will be understood that any shape or design can be used as desired. In some embodiments, the spikes 318 can be a predefined length and/or have marking as predefined lengths, such as 1 cm. As such, user can use the spikes to determine distances of object displayed on the screen. Although not illustrated in FIG. 3E, it will be understood that the opacity of the spikes can vary 318 as desired. In some embodiments, such as when the second affected region is a predicted affected region, as a dynamic affected region grows, the system can cause the spikes 318 to become transparent, or otherwise adjust a display setting, based at least in part on the location of the dynamic affected region with respect to the spikes 318. FIG. 3F illustrates an embodiment in which the embodiments from FIGS. 3B and 3E are combined. As mentioned previously, any combination of the described embodiments can be used as desired.

Figure 3G:
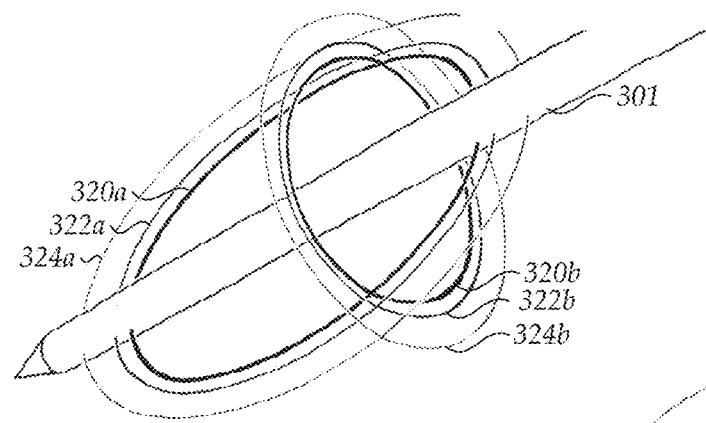

FIG. 3G illustrates embodiments in which portions of three affected regions are displayed as outlines 320a, 320b, 322a, 322b, 324a, 324b. In some embodiments, outlines 320a, 320b correspond to vertical and horizontal edges, respectively, of a first affected region, outlines 322a, 322b correspond to vertical and horizontal edges, respectively, of a second affected region, and outlines 324a, 324b correspond to vertical and horizontal edges, respectively, of a third affected region. FIG. 3G also illustrates embodiments in which the one or more outlines 320a, 320b, 322a, 322b, 324a, 324c are associated with a particular affected region, such as portions of a second affected region that are unique to it with respect to a first affected region.

Figure 3H:
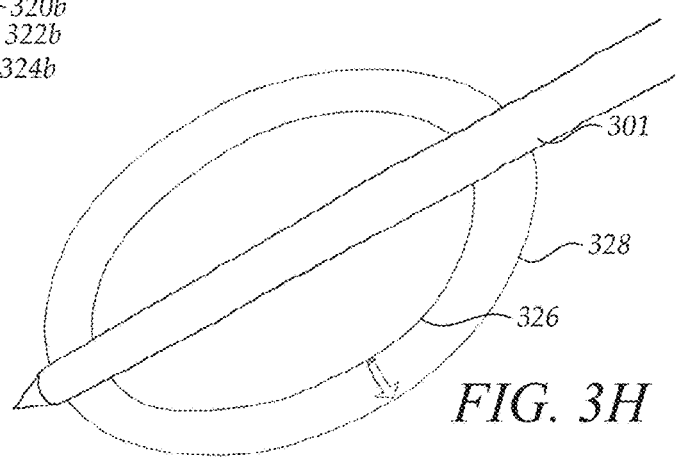

FIG. 3H illustrates an embodiment in which the two affected regions are displayed as two volumes 326, 328, in which the portions of the second affected region that are unique to the second affected region with respect to the first affected region are displayed differently (non-limiting examples: varying opacity, color, brightness, focus, etc.).

Figure 3I:
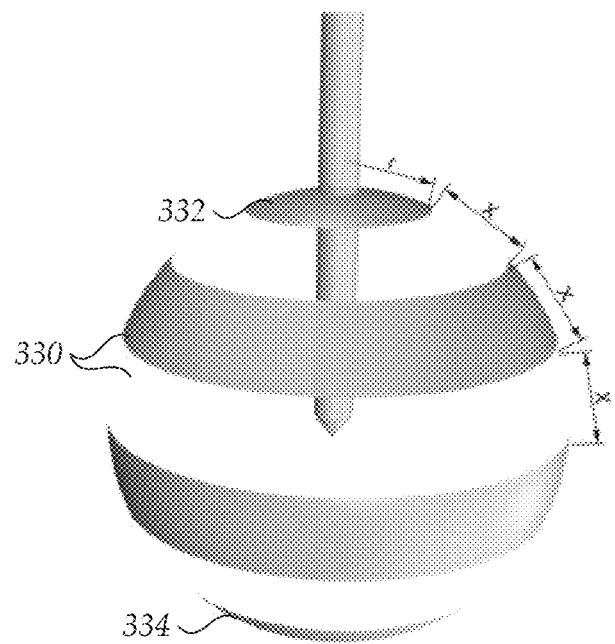

FIG. 3I illustrates embodiments in which portions of an affected region are displayed using horizontal bands 330 with alternating display settings (e.g., transparency, brightness, etc.). It will be understood that bands with any orientation can be used. Bands with higher transparency levels can enable a healthcare provider to see into the affected region. In some embodiments, the width and/or the arc length of each band can be equal, and a top portion 332 and a bottom portion 334 can have a variable corresponding width/arc length. As such, user can use the bands to determine distances of object displayed on the screen. The variable width/arc length can be determined such that the bands 330 have an equal width/arc length.

Figure 3J:
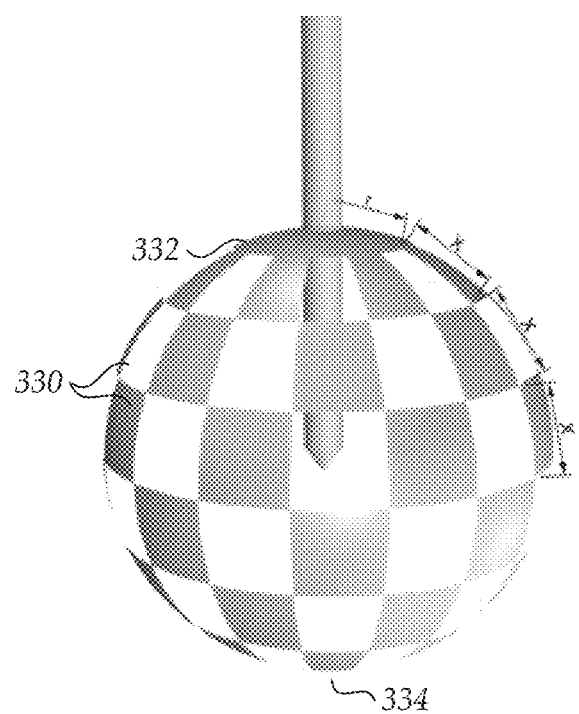

FIG. 3J illustrates an embodiment in which portions of an affected region are displayed using tiles 336 having alternating display settings (e.g., transparency, brightness, etc.). In some embodiments, each tile 336 can be displayed with a different display level. In certain embodiments, every other tile can be displayed with the same display level. Tiles with higher transparency levels can enable a healthcare provider to see into the affected region. In some embodiments, horizontal and/or vertical lengths and/or the arc length of each tile can be equal, and a top portion and a bottom portion can have a variable corresponding length. The variable length can be determined such that the tiles 336 have an equal length.

Surface Display Regions

FIGS. 4A-4C, and 5A-5C are diagrams showing various embodiments for displaying at least a portion of the affected regions that intersect with or are co-located or level with at least a portion of a medical display object (non-limiting examples: the image slice 302 (FIGS. 4A-4C) or the virtual medical device (FIGS. 5A and 5B)), which may also be referred to herein as surface display regions.

The surface display regions can correspond to predicted affected regions and/or dynamic affected regions, as desired. Accordingly, if the first and/or second affected regions are dynamic affected regions, the associated surface display regions can move, or grow, during operation of the medical device associated with the virtual medical device 401, 501.

In addition, the surface display regions can correspond to affected regions that are co-located with the medical display object or only portions thereof, or the medical display object's trajectory. Accordingly, in some embodiments, the surface display region can be displayed as a volume, area, or line depending on which portions of the affected region and medical display object are used to determine the surface display region.

In some embodiments, to determine whether a portion of the affected region and a portion of the medical display object are co-located or level, the system 100 can compare the coordinates of the portion of the affected region with the portion of the medical display object. If the coordinates (e.g., the x, y, z coordinates) match (e.g., are equal) or satisfy a distance threshold, the system can determine that the portion of the medical display object and the portion of the affected region are co-located. In certain embodiments, the system 100 can determine that the portion of the affected region and the portion of the medical display object are co-located if the portion of the affected region and the portion of the medical display object can be mapped to the same pixel in a video or image output data buffer.

The distance threshold can be a predefined distance, such as one or more bits, one or more pixels, etc. In some embodiments, the distance threshold can be based at least in part on whether the distance between the coordinates is perceptible to a user, which may be based at least in part on the size of the display, the size of the display relative to the image and/or imaged area, and/or the distance between the point-of-view location and the display, etc. For example, in some cases, the distance threshold can be smaller for larger displays (or larger display:image ratios) and larger for smaller displays (or smaller display:image ratios), or vice versa. In certain cases, the distance threshold can be larger for larger distances between the point-of-view location and the display and smaller for smaller distances between the point-of-view location and the display, or vice versa. In certain embodiments, the distance threshold can be different for each coordinate.

In certain embodiments, the system 100 can perform the comparison for each location of the medical display objects and/or each location of the affected regions. In some cases, the system can determine that the portion of the medical display object and the portion of the affected region are co-located if the portion of the medical display object and the portion of the affected region are level and have the same depth.

Any coordinate system can be used to compare the coordinates of the portion of the affected region with the medical display object and/or to determine whether the portion of the affected region is co-located with the medical display object. For example, the coordinate system of the display and/or the coordinate system of device in the system 100 that is used to determine the emplacement of the medical devices can be used, as desired.

In some embodiments, the coordinate system of the display is used. The coordinate system of the display can be any emplacement as desired. In certain embodiments, the coordinates of the display are that the x-axis is the width of the display, the y-axis is the height of the display, and the z-axis is the depth (e.g., into and out of) the display. In such embodiments, the system 100 can determine that the portion of the affected region satisfies the location threshold and/or is level with the medical display object, based at least in part on the x and y coordinates of the affected region and the x and y coordinates of the medical display object. For example, if the x and y coordinates of the affected region and the x and y coordinates of the medical display object match (or satisfy a distance threshold); the system 100 can determine that the portion of the affected region satisfies the location threshold.

Although reference is made to the x and y coordinates, it will be understood that the coordinates used to determine whether the portion of the affected region satisfies the location threshold and/or is co-located with the medical display object can be based at least in part on the coordinate system used. For example, in some embodiments, the coordinate system used can include the x-axis as the depth (e.g., forward/backward), the y-axis as lateral movement (e.g., side-to-side), and the z-axis as elevation (e.g., up/down). In such embodiments, the system 100 can determine that a portion of the affected region satisfies the location threshold if the y and z coordinates of the affected region match (or satisfy a distance threshold) the y and z coordinates of the medical display object.

In some embodiments, for each location on the display, the system can query whether a portion of the medical display object and/or a portion of the affected region have been (or will be) mapped to that location. If the system 100 determines that a portion of the medical display object and a portion of the affected region have been (or will be) mapped to that location, the system 100 can determine that the portion of the medical display object and the portion of the affected region are co-located.

In certain embodiments, the system 100 can determine that the portion of the affected region satisfies the location threshold, intersects, and/or is co-located with the medical display object if the portion of the affected region and the medical display object (or portion of the image corresponding to the medical display object) are co-located when mapped to a 2D plane. In some embodiments, the 2D plane can be based at least in part on the point-of-view location. For example, the 2D plane can be orthogonal to the point-of-view location. In certain embodiments, the system 100 can determine that the portion of the affected region satisfies the location threshold (or corresponding virtual affected region) if the portion of the affected region overlaps with the medical display object (or portion of the image corresponding to the medical display object) in a virtual image (e.g., one is directly in front of or behind the other in the virtual image). In certain embodiments, the system 100 can determine that the portion of the affected region satisfies the location threshold if the portion of the affected region and the medical display object (or portion of the image corresponding to the medical display object) map to the same location on a display, such as the same pixel or same array of pixels.

Figure 4A:
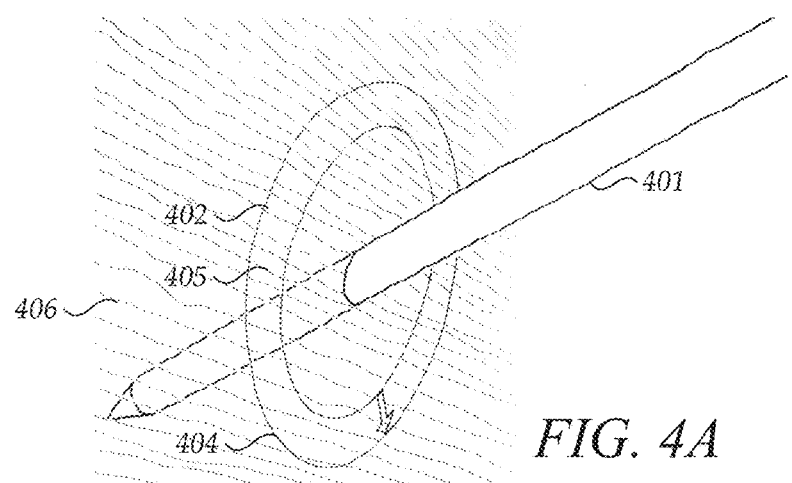
FIGS. 4A, 4B, and 4C are diagrams illustrating embodiments of surface display regions.
Figure 4B:
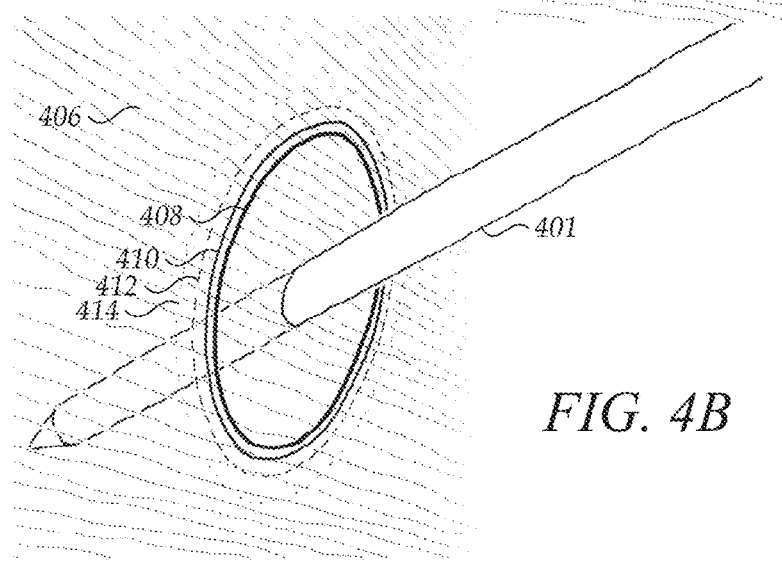
Figure 4C:
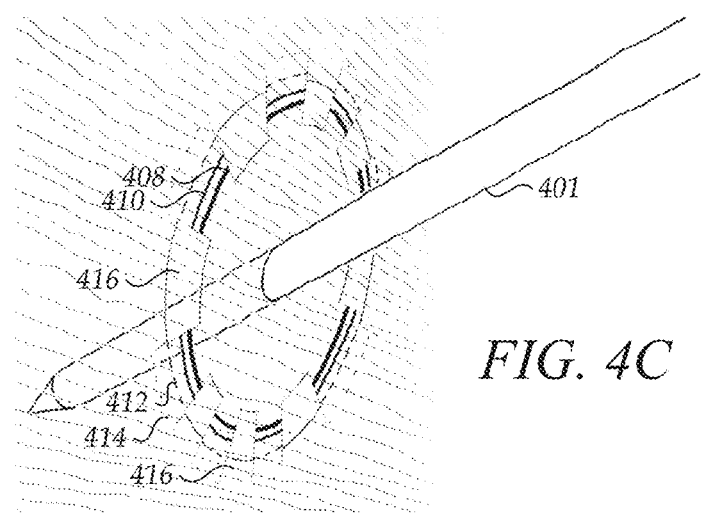

With continued reference to FIGS. 4A-4C, various embodiments of surface display regions are shown. It will be understood that the embodiments illustrated in FIGS. 4A-4C are non-limiting in nature. Furthermore, any portion of any of the embodiments described above with reference to FIGS. 3A-3J can be displayed in conjunction with any portion of the embodiments described below with reference to FIGS. 4A-4C.

FIG. 4A illustrates various embodiments including embodiments showing two surface display regions as lines 402, 404. The line 402 can correspond to an outline of a first affected region that is co-located with at least a portion of a virtual medical device (image slice 406) and the line 404 can correspond to an outline of a second affected region that is co-located at least a portion of the image slice 406. In some embodiments, the area between the lines 402, 404 can be displayed differently (non-limiting examples: varying opacity, color, brightness, focus, etc.). FIG. 4A can also illustrate embodiments showing a surface display region displayed as area 405. The area 405 can correspond to portions of a second affected region that are unique to it with respect to a first affected region and that are co-located with at least a portion of the image slice 406. In certain embodiments, the portions of the area 405 can be displayed differently (non-limiting examples: varying opacity, color, brightness, focus, etc.). FIG. 5A is similar to FIG. 4A except that the medical display object is the virtual medical device 501. Thus, lines 502, 504 correspond to lines 402, 404, respectively, and area 505 corresponds to area 405. In some embodiments lines 502, 505, and/or area 505 can correspond to portions of a second affected region that are co-located with at least a portion of the virtual medical device 501 and/or its trajectory.

FIG. 4B illustrates various embodiments showing multiple solid lines 408, 410 and dashed lines 412, 414, which can form part of one or more surface display regions. For example, lines 408, 410 can correspond different portions of a first affected region (and form part of a first surface display region) and lines 412, 414 can correspond to different portions of a second affected region (and form part of a surface display region). In some embodiments, line 408 forms part of a first surface display region and lines 410, 412, 414 form part of a second surface display region, such as portions of the second affected region that are unique to it with respect to the first affected region. In certain embodiments, lines 408, 410, 412, 414 form part of four surface display regions. FIG. 5A is similar to FIG. 4A except that the medical display object is the virtual medical device 501. Thus, lines 508, 510, 512, 514 correspond to lines 408, 410, 412, 414, respectively, and area 505 corresponds to area 405.

FIG. 4C illustrates an embodiment in which an additional surface display region is displayed with the surface display regions illustrated in FIG. 4B. In an embodiment, line 408 forms part of a first surface display region that corresponds to a first predicted affected region and lines 410, 412, 414 form part of a second surface display region that corresponds to a second predicted affected region. Indicators 416 form part of a third surface display region, which corresponds to a dynamic affected region. As such, during operation of the medical device that corresponds to the virtual medical device 401, lines 408, 410, 412, and 414 can remain static, while indicators 416 move outward. In this manner, a healthcare provider can determine at what point to terminate operation of the medical device. Although a corresponding FIG. 5 is not provided, it will be understood that the medical display object can correspond to any object displayed by a display.

It will be understood that any of the aforementioned embodiments from FIGS. 3A-3J, 4A-4C, 5A, and 5B can be combined as desired. For example, FIG. 5C is a diagram illustrating an embodiment in which the embodiments described above with reference to FIGS. 3D, 3G, 4C, and 5B are combined.

Figure 6:
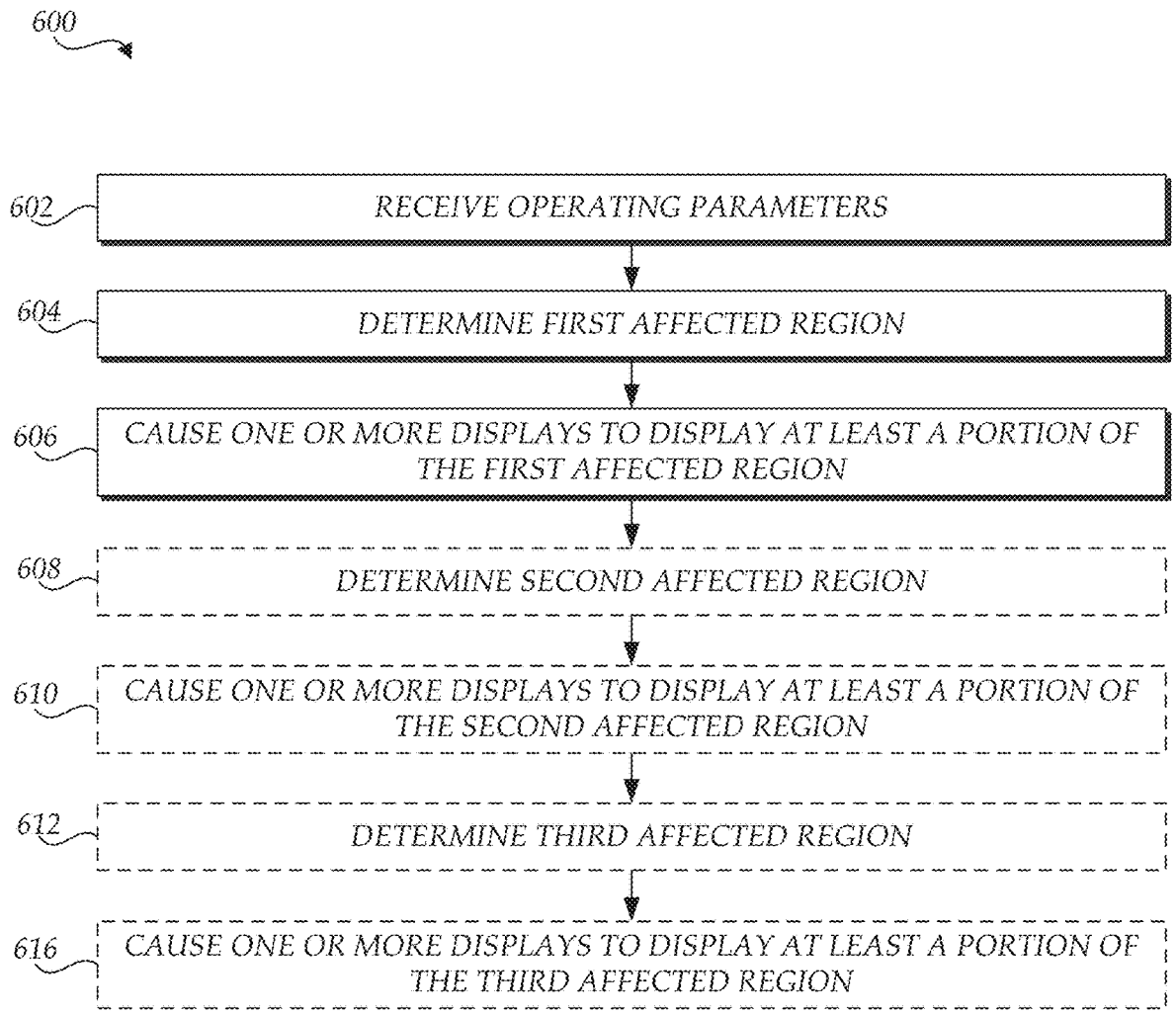
FIG. 6 is a flow diagram illustrative of an embodiment of a routine implemented by the system to display a displayed affected region.

FIG. 6 is a flow diagram illustrative of an embodiment of a routine 600 implemented by the system 100 to display at least a portion of an affected region, or displayed affected region. One skilled in the relevant art will appreciate that the elements outlined for routine 600 can be implemented by one or more computing devices/components that are associated with the system 100, such as the position sensing unit 140, the image guidance unit 130, surgical system 149, and/or imaging unit 150. Accordingly, routine 600 has been logically associated as being generally performed by the system 100. However, the following illustrative embodiment should not be construed as limiting. Furthermore, it will be understood that the various blocks described herein with reference to FIG. 6 can be implemented in a variety of orders. For example, the system may implement some blocks concurrently or change the order, as desired.

At block 602, the system 100 receives operating parameters of a medical device. As described in greater detail above, the operating parameters can include information regarding make and model, power and duration settings of the medical device, and/or variance parameters, etc. The operating parameters can be stored in a non-transitory, computer-readable medium associated with the system 100 and/or can be stored in the medical device.

At block 604, the system 100 determines a first affected region. As described previously, affected regions can correspond to predicted affected regions and/or a dynamic affected regions. In some embodiments, the system determines the first affected region based at least in part on the operating parameters and/or measured parameters. In certain embodiments, the system 100 determines the first affected region based at least in part on a variance parameter of the medical device.

At block 606, the system 100 causes one or more displays to display at least a portion of the first affected region, or first displayed affected region. As described previously, the first displayed affected region can be displayed in a 2D view or 3D view and/or as a perspective view.

In addition, as described in greater detail above, the displayed affected region can be displayed as a volume, area, and/or line. The displayed affected region can be wireframed, transparent, semi-transparent, have varied opacity, brightness, and/or focus, include alternating bands/tiles, be textured, include solid or dashed lines, include spikes, etc. In certain embodiments, the at least a portion of the first affected region corresponds to portions of the first affected region that are unique to it, with respect to other affected regions. In some embodiments, the displayed affected region corresponds to at least a portion of the first affected region that is co-located with at least a portion of a medical display object (non-limiting examples: a virtual medical device, image slice, etc.) or its trajectory, also referred to as the surface display region.

It will be understood that fewer, more, or different blocks can be used as part of the routine 600. For example, any combination of blocks 608, 610, 612, and 614 can be included as part of routine 600.

At block 608, the system 100 determines a second affected region. The second affected region can be determined in a manner similar to the first affected region. As described in greater detail above, in some embodiments, the variance parameter can be used to determine the first and second affected regions. For example, a first variance threshold can be used to determine the first affected region and a second variance threshold can be used to determine the second affected region. In certain cases, the first variance threshold can be less than the second variance threshold. In such embodiments, the second affected region can be larger than, and in some cases include, the first affected region.

At block 610, the system 100 causes one or more displays to display at least a portion of the second affected region, or second displayed affected region. The system 100 can cause the one or more displays to display the second displayed affected region similar to the first displayed affected region. In some embodiments, the second displayed affected region can be displayed differently, such as by using a different color, transparency level, focus setting, shape, texture, etc. Furthermore, in some embodiments, the system can omit causing the display of the first displayed affected region in favor of the second displayed affected region. In such embodiments, the second displayed affected region can, in some instances, correspond to the portions of the second affected region that are unique to the second affected region, with respect to the first affected region.

In some instances the first affected region can be a predicted affected region and the second affected region can be a dynamic affected region. As such, in certain embodiments, during operation of the medical device, the second displayed affected region can change and/or grow with respect to the first displayed affected region.

At block 612, the system 100 determines a third affected region. For example, in some embodiments, the first and second affected regions can be first and second predicted affected regions and the third affected region can be a dynamic affected region. However, in certain embodiments the three affected regions can be dynamic affected regions, predicted affected regions, or any combination thereof.

At block 614, the system 100 causes one or more displays to display at least a portion of the third affected region, or third displayed affected region. The system 100 can cause the one or more displays to display the third displayed affected region similar to the first and second displayed affected regions. In some embodiments, the third displayed affected region can be displayed differently, such as by using a different color, transparency level, focus setting, shape, texture, etc. In embodiments, where the third affected region is a dynamic affected region and the first and second affected regions are predicted affected regions, the third displayed affected region can move with respect to the first and second displayed affected regions.

With continued reference to FIG. 6, it will be understood that fewer or more blocks can be included. For example, as described in greater detail above, the system 100 can receive emplacement data from one or more sensors corresponding to one or more medical devices, determine a emplacement of the medical devices and/or corresponding virtual medical devices (as a non-limiting example, the emplacement can be determined based at least in part on a point-of-view location), cause one or more displays to display the virtual medical devices and/or perspective views thereof, determine emplacement of the affected regions with respect to the virtual medical devices, determine emplacement of and display an image slice, alter the display of the image slice, display the medical display objects in a 2D view, a 3D view, and/or a perspective view, etc.

Figure 7:
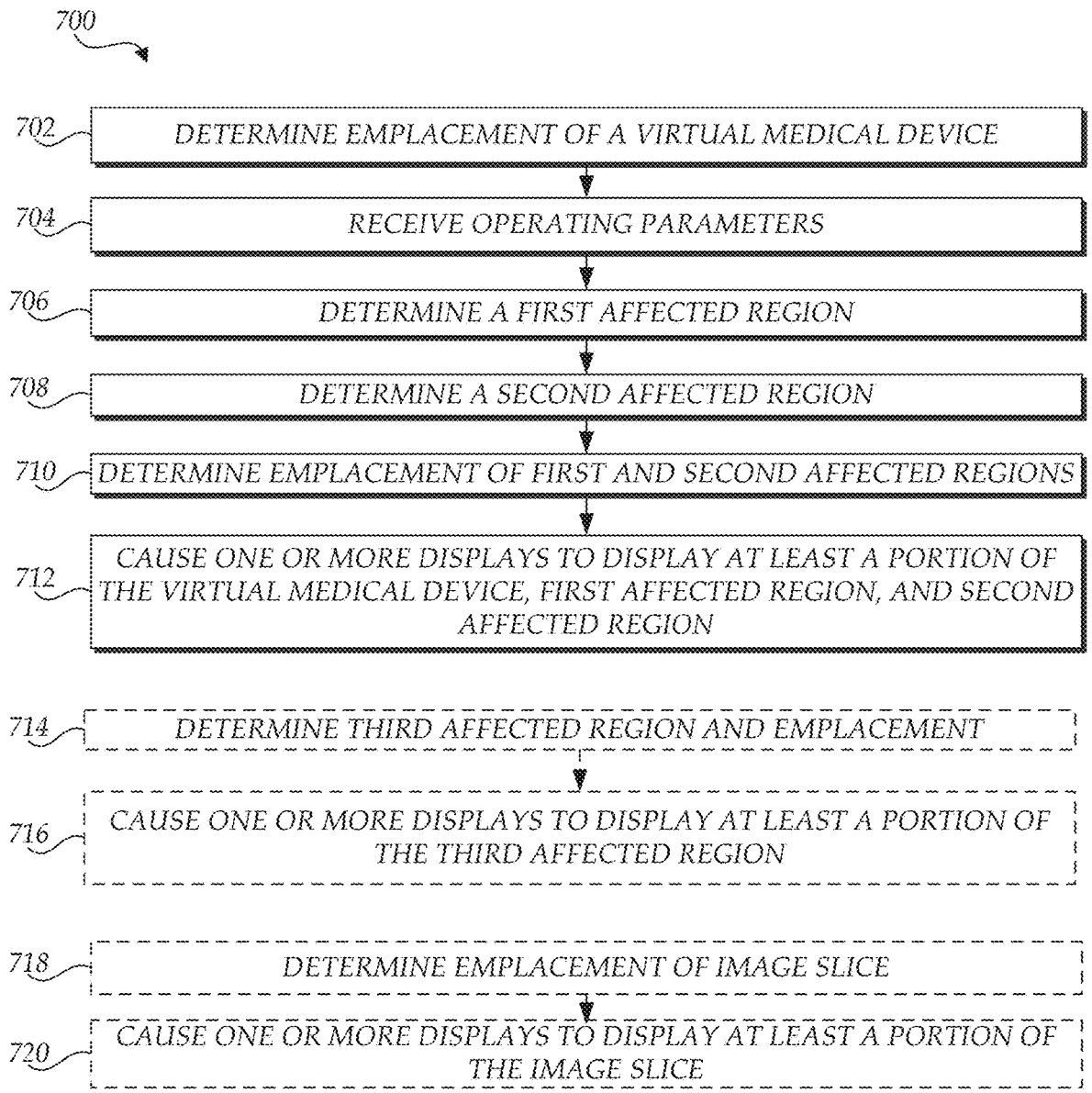
FIG. 7 is a flow diagram illustrative of an embodiment of a routine implemented by the system to display displayed affected regions.

FIG. 7 is a flow diagram illustrative of an embodiment of a routine 700 implemented by the system 100 to display at least a portion of multiple affected regions, or multiple displayed affected regions. One skilled in the relevant art will appreciate that the elements outlined for routine 700 can be implemented by one or more computing devices/components that are associated with the system 100, such as the position sensing unit 140, the image guidance unit 130, surgical system 149, and/or imaging unit 150. Accordingly, routine 700 has been logically associated as being generally performed by the system 100. However, the following illustrative embodiment should not be construed as limiting. Furthermore, it will be understood that the various blocks described herein with reference to FIG. 7 can be implemented in a variety of orders. For example, the system may implement some blocks concurrently or change the order, as desired.

At block 702, the system 100 determines the emplacement of a virtual medical device. In some embodiments, as described above, the system 100 can determine the emplacement of the virtual medical device based at least in part on emplacement data corresponding to a medical device, such as medical device 242. As described previously, the emplacement data can be received from one or more emplacement sensors associated with the medical device.

At block 704, the system 100 obtains operating parameters of the medical device, as described in greater detail above with reference to block 602 of FIG. 6. At block 706, the system 100 determines a first affected region. In some embodiments, the system 100 can determine the first affected region similar to the determination of the first affected region referenced above with respect to block 604 of FIG. 6. At block 708, the system 100 determines a second affected region. In some embodiments, the system 100 can determine the second affected region similar to the determination of the second affected region referenced above with respect to block 608 of FIG. 6. As described in greater detail above the first and second affected regions can be predicted affected regions and/or dynamic affected regions, as desired.

At block 710, the system 100 can determine the emplacement of the first and second affected regions. At block 712, the system 100 can cause one or more displays to display at least a portion of the virtual medical device, at least a portion of the first affected region (second displayed affected region), and at least a portion of the second affected region (second displayed affected region). As described previously, the displayed affected regions can, in some embodiments, correspond to surface display regions. In some embodiments, the system 100 can cause the one or more displays to display at least a portion of the first and second affected regions similar to blocks 606 and 610 of FIG. 6, described previously. As described above, the first and second displayed affected regions can be displayed in a variety of ways.

It will be understood that fewer, more, or different blocks can be used as part of the routine 700. For example, any combination of blocks 714, 716, 718, and 720 can be included as part of routine 700.

At block 714, the system 100 can determine a third affected region, and at block 716, the system 100 can cause the one or more displays to display at least a portion of the third affected region. In some embodiments, the system 100 can determine the third affected region and display a third displayed affected region similar to the first and second displayed affected regions as described in greater detail above with reference to blocks 612 and 616 of FIG. 6. In certain embodiments, the third displayed affected region can be a surface display region.

At block 718, the system 100 can determine an emplacement of an image slice, and at block 720, the system 100 can cause the one or more displays to display at least a portion of the image slice and/or perspective view thereof, as described in greater detail above.

With continued reference to FIG. 7, it will be understood that fewer or more blocks can be included. For example, as described in greater detail above, the system 100 can receive emplacement data from one or more sensors associated with one or more medical devices, display additional displayed affected regions, alter the display of the image slice, display image guidance cues, display the medical display objects in a 2D view, a 3D view, and/or a perspective view, etc.

Terminology

Those having skill in the art will further appreciate that the various illustrative logical blocks, modules, circuits, and process steps described in connection with the implementations disclosed herein can be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans can implement the described functionality in varying ways for each particular application, but such implementation decisions should not be interpreted as causing a departure from the scope of the present invention. One skilled in the art will recognize that a portion, or a part, can comprise something less than, or equal to, a whole. For example, a portion of a collection of pixels can refer to a sub-collection of those pixels.

The various illustrative logical blocks, modules, and circuits described in connection with the implementations disclosed herein can be implemented or performed with a processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A processor can be a microprocessor, but in the alternative, the processor can be any conventional processor, controller, or microcontroller. A processor can also be implemented as a combination of computing devices, e.g., a combination of a DSP and a microprocessor, a plurality of microprocessors, one or more microprocessors in conjunction with a DSP core, or any other such configuration.

The steps of a method or process described in connection with the implementations disclosed herein can be embodied directly in hardware, in a software module executed by a processor, or in a combination of the two. A software module can be stored in RAM memory, flash memory, ROM memory, EPROM memory, EEPROM memory, registers, hard disk, a removable disk, a CD-ROM, or any other form of non-transitory computer-readable medium known in the art, as computer-executable instructions. An exemplary computer-readable storage medium is coupled to the processor such the processor can read information and/or computer-executable instructions from, and write information to, the computer-readable storage medium. In the alternative, the storage medium can be integral to the processor. The processor and the storage medium can reside in an ASIC. The ASIC can reside in a user terminal, camera, or other device. In the alternative, the processor and the storage medium can reside as discrete components in a user terminal, camera, or other device.

Headings are included herein for reference and to aid in locating various sections. These headings are not intended to limit the scope of the concepts described with respect thereto. Such concepts can have applicability throughout the entire specification.

Conditional language such as, among others, "can," "could," "might" or "may," unless specifically stated otherwise, are otherwise understood within the context as used in general to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

Language such as the phrase "at least one of X, Y and Z," and "at least one of X, Y or Z," unless specifically stated otherwise, is understood with the context as used in general to convey that an item, term, etc. may be either X, Y or Z, or any combination thereof. Thus, such language is not generally intended to imply that certain embodiments require at least one of X, at least one of Y and at least one of Z to each be present or exclusively X or exclusively Y or exclusively Z.

Unless otherwise explicitly stated, articles such as 'a' or 'an' should generally be interpreted to include one or more described items. Accordingly, phrases such as "a device configured to" are intended to include one or more recited devices. Such one or more recited devices can also be collectively configured to carry out the stated recitations. For example, "a processor configured to carry out recitations A, B and C" can include a first processor configured to carry out recitation A working in conjunction with a second processor configured to carry out recitations B and C.

The previous description of the disclosed implementations is provided to enable any person skilled in the art to make or use the present invention. Various modifications to these implementations will be readily apparent to those skilled in the art, and the generic principles defined herein can be applied to other implementations without departing from the spirit or scope of the invention. Furthermore, although described above with reference to medical devices and procedures, it will be understood that the embodiments described herein can be applied to other systems in which objects are tracked and virtual representations are displayed on a display and/or systems in which multiple objects are displayed on a display within a virtual space, such as within a virtual 3D space. Thus, the present invention is not intended to be limited to the implementations shown herein but is to be accorded the widest scope consistent with the principles and novel features disclosed herein.

The invention claimed is:

1. A method, comprising:
receiving first emplacement data corresponding to a medical device;
determining an emplacement of a virtual medical device with respect to a point-of-view location based at least in part on the first emplacement data, wherein the virtual medical device corresponds to the medical device;
receiving operating parameters corresponding to the medical device;
determining a first predicted affected region based at least in part on the operating parameters and a predicted advancement of the medical device along a forward trajectory, wherein the operating parameters comprise a variance parameter that corresponds to a margin of error associated with said determining the first predicted affected region;
determining a second predicted affected region based at least in part on the variance parameter; and
causing one or more displays to display:
a perspective view of at least a portion of the virtual medical device,
a perspective view of the first predicted affected region, and
a perspective view of the second predicted affected region.

2. The method of claim 1, further comprising determining an emplacement of the first predicted affected region, wherein causing the one or more displays to display the perspective view of the first predicted affected region comprises causing the one or more displays to display the perspective view of the first predicted affected region based at least in part on the determined emplacement of the first predicted affected region.

3. The method of claim 1, wherein determining the first predicted affected region comprises determining the first predicted affected region based at least in part on the variance parameter.

4. The method of claim 1, wherein the second predicted affected region is smaller than the first predicted affected region.

5. The method of claim 4, further comprising determining a third predicted affected region based at least in part on the variance parameter, wherein the third predicted affected region is larger than the first predicted affected region.

6. The method of claim 5, wherein the variance parameter comprises a first threshold and a second threshold, the second threshold being greater than the first threshold, wherein the first threshold is used to determine the second predicted affected region and the second threshold is used to determine the third predicted affected region.

7. The method of claim 5, further comprising:
causing the one or more displays to display:
a perspective view of the second predicted affected region; and
a perspective view of the third predicted affected region.

8. The method of claim 1, wherein the point-of-view location comprises at least one of a location of a user, an expected location of the user, or a fixed location relative to the one or more displays.

9. The method of claim 1, wherein the medical device comprises an ablation needle and the operating parameters comprise at least one of a power level of the ablation needle, a duration setting of the ablation needle, or a model of the ablation needle.

10. A system, comprising:
one or more processors communicatively coupled with one or more displays, and a non-transitory computer-readable storage medium storing computer-executable instructions that when executed by the one or more processors cause the one or more processors to:
receive first emplacement data corresponding to a medical device;
determine an emplacement of a virtual medical device with respect to a point-of-view location based at least in part on the first emplacement data, wherein the virtual medical device corresponds to the medical device;
receive operating parameters corresponding to the medical device;
determine a first predicted affected region based at least in part on the operating parameters and a predicted advancement of the medical device along a forward trajectory, wherein the operating parameters comprise a variance parameter that corresponds to a margin of error associated with the determination of the first predicted affected region;
determine a second predicted affected region based at least in part on the variance parameter; and
cause the one or more displays to display:
a perspective view of at least a portion of the virtual medical device,
a perspective view of the first predicted affected region, and
a perspective view of the second predicted affected region.

11. The system of claim 10, wherein the computer-executable instructions when executed further cause the one or more processors to determine an emplacement of the first predicted affected region, wherein to cause the one or more displays to display the perspective view of the first predicted affected region, the computer-executable instructions further cause the one or more processors to cause the one or more displays to display the perspective view of the first predicted affected region based at least in part on the determined emplacement of the first predicted affected region.

12. The system of claim 10, wherein the variance parameter comprises a first threshold and a second threshold, the second threshold being greater than the first threshold.

13. The system of claim 12, wherein the computer-executable instructions when executed further cause the one or more processors to:
determine the second predicted affected region based at least in part on the first threshold, wherein the second predicted affected region is smaller than the first predicted affected region;
determine a third predicted affected region based at least in part on the second threshold, wherein the third predicted affected region is larger than the first predicted affected region; and
cause the one or more displays to display a perspective view of the third predicted affected region.

14. The system of claim 10, wherein the point-of-view location comprises at least one of a location of a user, an expected location of the user, or a fixed location relative to the one or more displays.

15. The system of claim 10, wherein the medical device comprises an ablation needle and the operating parameters comprise at least one of a power level of the ablation needle, a duration setting of the ablation needle, or a model of the ablation needle.

16. A computer-readable, non-transitory storage medium storing computer-executable instructions that when executed by one or more processors cause the one or more processors to:
receive first emplacement data corresponding to a medical device;
determine an emplacement of a virtual medical device with respect to a point-of-view location based at least in part on the first emplacement data, wherein the virtual medical device corresponds to the medical device;
receive operating parameters corresponding to the medical device;
determine a first predicted affected region based at least in part on the operating parameters and a predicted advancement of the medical device along a forward trajectory, wherein the operating parameters comprise a variance parameter that corresponds to a margin of error associated with said determining the first predicted affected region;
determine a second predicted affected region based at least in part on the variance parameter; and
cause one or more displays to display:
a perspective view of at least a portion of the virtual medical device,
a perspective view of the first predicted affected region, and
a perspective view of the second predicted affected region.

17. The computer-readable, non-transitory storage medium of claim 16, wherein the computer-executable instructions when executed further cause the one or more processors to determine an emplacement of the first predicted affected region, wherein to cause the one or more displays to display the perspective view of the first predicted affected region, the computer-executable instructions further cause the one or more processors to cause the one or more displays to display the perspective view of the first predicted affected region based at least in part on the determined emplacement of the first predicted affected region.

18. The computer-readable, non-transitory storage medium of claim 16, wherein the variance parameter comprises a first threshold and a second threshold, the second threshold being greater than the first threshold.

19. The computer-readable, non-transitory storage medium of claim 18, wherein the computer-executable instructions when executed further cause the one or more processors to:
determine the second predicted affected region based at least in part on the operating parameters and the first threshold, wherein the second predicted affected region is smaller than the first predicted affected region;
determine a third predicted affected region based at least in part on the operating parameters and the second threshold, wherein the third predicted affected region is larger than the first predicted affected region; and
cause the one or more displays to display a perspective view of the third predicted affected region.

20. The computer-readable, non-transitory storage medium of claim 16, wherein the medical device comprises an ablation needle and the operating parameters comprise at least one of a power level of the ablation needle, a duration setting of the ablation needle, or a model of the ablation needle.

\* \* \* \* \*